(12) United States Patent
Gross et al.

(10) Patent No.: US 10,738,269 B2
(45) Date of Patent: *Aug. 11, 2020

(54) PHOTOBIOREACTOR SYSTEMS AND METHODS

(71) Applicants: Gross-Wen Technologies, Inc., Ames, IA (US); Iowa State University Research Foundation, Inc., Ames, IA (US)

(72) Inventors: Martin Anthony Gross, Ames, IA (US); Zhiyou Wen, Ames, IA (US)

(73) Assignees: Gross-Wen Technologies, Inc., Ames, IA (US); Iowa State University Research Foundation, Inc., Ames, IA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/587,628

(22) Filed: Sep. 30, 2019

(65) Prior Publication Data

US 2020/0024559 A1 Jan. 23, 2020

Related U.S. Application Data

(63) Continuation of application No. 16/230,036, filed on Dec. 21, 2018, now Pat. No. 10,570,359, which is a (Continued)

(51) Int. Cl.
| | | |
|---|---|---|
| *C12M 1/00* | (2006.01) | |
| *C12N 11/02* | (2006.01) | |
| *C12N 11/14* | (2006.01) | |
| *C12N 1/12* | (2006.01) | |
| *C12M 1/12* | (2006.01) | |
| *C12M 3/06* | (2006.01) | |

(52) U.S. Cl.
CPC ............ *C12M 21/02* (2013.01); *C12M 25/02* (2013.01); *C12M 27/14* (2013.01); *C12N 1/12* (2013.01); *C12N 11/02* (2013.01); *C12N 11/14* (2013.01)

(58) Field of Classification Search
CPC ...... C12M 21/02; C12M 25/02; C12M 27/14; C12N 1/20; C12N 1/12; C12N 11/02; C12N 11/14
See application file for complete search history.

(56) References Cited

U.S. PATENT DOCUMENTS

| | | | | |
|---|---|---|---|---|
| 4,324,068 A | * | 4/1982 | Anthony ................ | C12M 21/02 47/1.4 |
| 9,932,549 B2 | * | 4/2018 | Gross ..................... | C12N 11/02 |

(Continued)

*Primary Examiner* — William H. Beisner
*Assistant Examiner* — Danielle B Henkel
(74) *Attorney, Agent, or Firm* — Ulmer & Berne LLP

(57) ABSTRACT

An algal growth system includes a first flexible sheet material mounted on a first frame in a first mounted geometry having a first height and a first width, the first height being greater than the first width, and a second flexible sheet material mounted on a second frame in a second mounted geometry having a second height and a second width, the second height being greater than the second width. The first flexible sheet and the second flexible sheet material are noncontiguous. The algal growth system also includes a motor, the motor being coupled with an actuator system, where the motor actuates the actuator system, and a reservoir.

20 Claims, 21 Drawing Sheets

Related U.S. Application Data continuation of application No. 15/920,304, filed on Mar. 13, 2018, now abandoned, which is a continuation of application No. 14/214,390, filed on Mar. 14, 2014, now Pat. No. 9,932,549.

(60) Provisional application No. 61/783,737, filed on Mar. 14, 2013.

(56) References Cited

U.S. PATENT DOCUMENTS

| | | | |
|---|---|---|---|
| 10,125,341 B2 * | 11/2018 | Wen | C12M 27/14 |
| 10,570,359 B2 * | 2/2020 | Gross | C12N 11/02 |
| 2010/0224574 A1 * | 9/2010 | Youngs | B01D 33/42 |
| | | | 210/783 |
| 2011/0217764 A1 * | 9/2011 | Christenson | C12M 1/10 |
| | | | 435/289.1 |
| 2011/0258915 A1 * | 10/2011 | Subhadra | C12P 7/6472 |
| | | | 44/385 |
| 2011/0312062 A1 * | 12/2011 | Nordvik | C12M 25/01 |
| | | | 435/257.1 |

* cited by examiner

PHOTOBIOREACTOR SYSTEMS AND METHODS

REFERENCE TO RELATED APPLICATIONS

The present application is a continuation of U.S. patent application Ser. No. 16/230,036, filed Dec. 21, 2018, now U.S. Pat. No. 10,570,359, issued Feb. 25, 2020, which is a continuation of U.S. patent application Ser. No. 15/920,304, filed Mar. 13, 2018, which is a continuation of U.S. patent application Ser. No. 14/214,390, filed Mar. 14, 2014, now U.S. Pat. No. 9,932,549, issued Apr. 3, 2018, which claims the priority benefit of U.S. Provisional Patent Application No. 61/783,737, filed Mar. 14, 2013, and hereby incorporates the same applications herein by reference in their entireties.

TECHNICAL FIELD

Embodiments of the technology relate, in general, to biofilm technology, and in particular to a revolving algal biofilm (RAB) photobioreactor for stimulating algal growth and simplified biomass harvesting.

BRIEF DESCRIPTION OF THE DRAWINGS

The present disclosure will be more readily understood from a detailed description of some example embodiments taken in conjunction with the following figures.

SUMMARY

Figure 1:
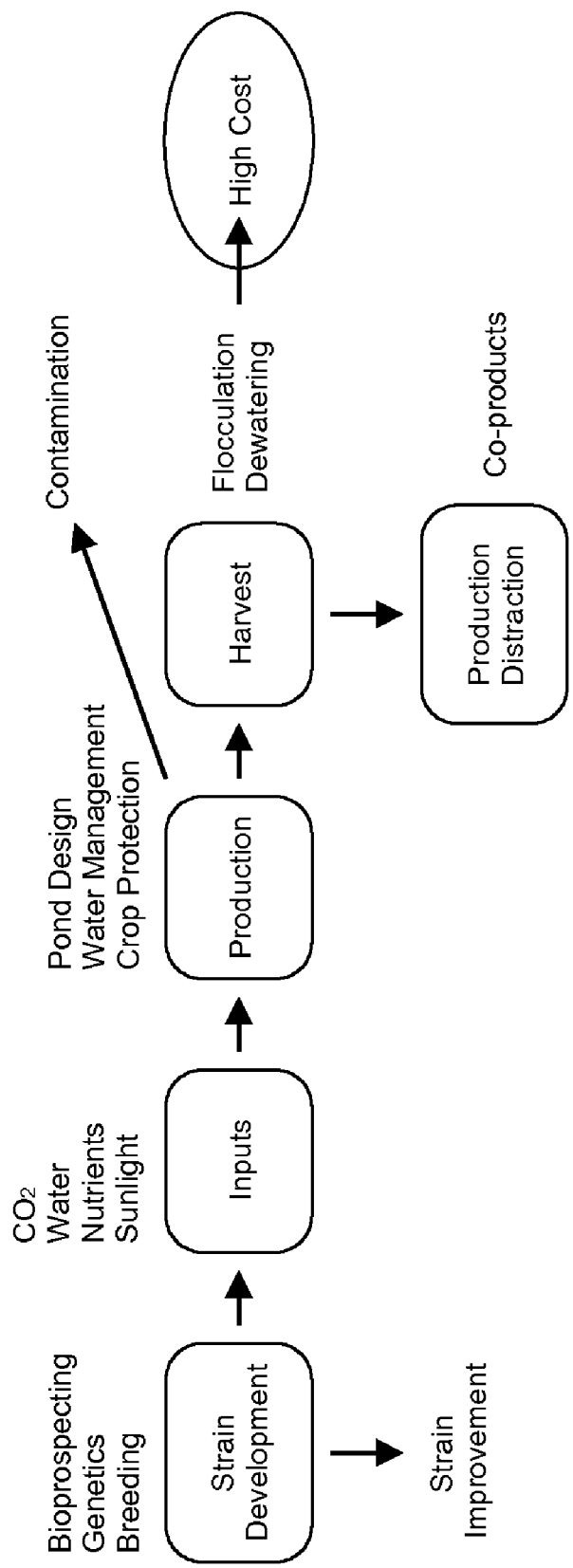
FIG. 1 depicts a flow chart illustrating the methodology generally associated with algae harvesting.

An algal growth system can include a frame and a flexible sheet material that can have a substantially vertical orientation, where the flexible sheet material can be configured to facilitate the growth and attachment of algae, where the flexible sheet material can be supported by the frame. The algal growth system can include a first drive shaft, where the first drive shaft can be coupled with the frame, where the first drive shaft can support and actuate the flexible sheet material, a gear system, where the gear system can be coupled with the first drive shaft, a first roller, where the first roller can be coupled with the frame and can be configured to guide the flexible sheet material, and a drive motor, where the drive motor can be coupled with the gear system, where the drive motor can actuate the gear system and the at least one drive shaft such that the flexible sheet material can be actuated.

A method of growing algae can include the step of providing an algal growth system that can include a frame and a flexible sheet material that can have a substantially vertical orientation, where the flexible sheet material can be configured to facilitate the growth and attachment of algae, where the flexible sheet material can be supported by the frame. The algal growth system can include a first drive shaft, where the first drive shaft can be coupled with the frame, where the first drive shaft can support and actuate the flexible sheet material, a gear system, where the gear system can be coupled with the first drive shaft, a first roller, where the first roller can be coupled with the frame and can be configured to guide the flexible sheet material, and a drive motor, where the drive motor can be coupled with the gear system, where the drive motor can actuate the gear system and the at least one drive shaft such that the flexible sheet material can be actuated. The method for growing algae can include the steps of providing a liquid reservoir containing a contacting liquid, rotating the flexible sheet material of the algal growth system through a liquid phase, rotating the flexible sheet material of the algal growth system through a gaseous phase, and harvesting the algae from the flexible sheet material.

DETAILED DESCRIPTION

Various non-limiting embodiments of the present disclosure will now be described to provide an overall understanding of the principles of the structure, function, and use of the proficiency tracking systems and processes disclosed herein. One or more examples of these non-limiting embodiments are illustrated in the accompanying drawings. Those of ordinary skill in the art will understand that systems and methods specifically described herein and illustrated in the accompanying drawings are non-limiting embodiments. The features illustrated or described in connection with one non-limiting embodiment may be combined with the features of other non-limiting embodiments. Such modifications and variations are intended to be included within the scope of the present disclosure.

Reference throughout the specification to "various embodiments," "some embodiments," "one embodiment," "some example embodiments," "one example embodiment," or "an embodiment" means that a particular feature, structure, or characteristic described in connection with any embodiment is included in at least one embodiment. Thus, appearances of the phrases "in various embodiments," "in some embodiments," "in one embodiment," "some example embodiments," "one example embodiment," or "in an embodiment" in places throughout the specification are not necessarily all referring to the same embodiment. Furthermore, the particular features, structures or characteristics may be combined in any suitable manner in one or more embodiments.

Traditionally, algae are grown in open raceway ponds or enclosed photobioreactors, where algae cells are in suspension and are harvested through sedimentation, filtration, or centrifugation. Due to the light penetration problem caused by mutual shading of suspended algal cells, the algal growth in suspension is often limited by light availability. Also, due to the small size (3-30 µm) of algae cells and the dilute algae concentration (<1% w/v), gravity sedimentation of suspended cells often takes a long time in a large footprint settling pond. Filtration of algal cells from the culture broth can result in filter fouling. Centrifugation can achieve high harvest efficiency; however, the capital investment and operational cost for a centrifugation system can be prohibitively expensive. Due to these drawbacks, an alternative method for growing and harvesting algae biomass may be advantageous.

Described herein are example embodiments of revolving algal biofilm photobioreactor systems and methods that can enhance cell growth and simplify biomass harvesting. In one example embodiment, systems and methods can provide cost effective harvesting of algae biomass. In some embodiments, systems and methods can be used to produce algae for biofuel feedstock, and aquacultural feed, and nutraceuticals. In some embodiments, algal cells can be attached to a material that can be rotated between a nutrient-rich liquid phase and a carbon dioxide rich gaseous phase such that alternative absorption of nutrients and carbon dioxide can occur. The algal cells can be harvested by scraping from the surface to which they are attached, which can eliminate harvest procedures commonly used in suspension cultivation systems, such as sedimentation, flocculation, floatation, and/or centrifugation. It will be appreciated that systems and methods described herein can be combined with sedimentation, centrifugation, or any other suitable processes.

The examples discussed herein are examples only and are provided to assist in the explanation of the apparatuses, devices, systems and methods described herein. None of the features or components shown in the drawings or discussed below should be taken as mandatory for any specific implementation of any of the apparatuses, devices, systems or methods unless specifically designated as mandatory. For ease of reading and clarity, certain components, modules, or methods may be described solely in connection with a specific figure. Any failure to specifically describe a combination or sub-combination of components should not be understood as an indication that any combination or sub-combination is not possible. Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

Example embodiments described herein can mitigate air and water pollution while delivering high value bio-based products such as bio-fuels, nutraceuticals, and animal feeds from microalgae. Example embodiments of RAB technology can play a beneficial role in creating an algal culture system that can economically produce algae biomass for, for example, biofuels, nutraceuticals, and animal feeds. Microalgae may have a significant impact in the renewable transportation fuels sector. Example embodiments can grow microalgae that can be used in biofuel production with a low harvest cost. Algae, if produced economically, may also serve as a primary feed source for nutraceuticals and aqua feeds production.

Example systems and methods can include developing a biofilm-based microalgae cultivation system (RAB) that could be widely adapted by the microalgae industry for producing, for example, fuels and high value products, as well as for treating municipal, industrial, and agricultural wastewater. Microalgae use photosynthesis to transform carbon dioxide and sunlight into energy. This energy is stored in the cell as oil, which has a high energy content. The oil yield from algae can be significantly higher than that from other oil crops. Algae oil can generally be easily converted to biodiesel and could replace traditional petroleum-based diesel. In addition to fuel production, microalgae have also been rigorously researched for the potential to produce various high value products such as animal feed, omega-3 polyunsaturated fatty acids, pigments, and glycoproteins.

Referring to FIG. 1, low biomass productivity and high cost of algae production can still be the major limitation in industrial scale operation. Example embodiments described herein may minimize such costs associated with the growth and harvesting of algal cells from an aqueous culture system.

Generally, research on algae cultivation is done using suspended algae culture. This culture method can have drawbacks including low biomass yield and productivity and low efficiency of harvesting the algal cells from liquid culture medium. Example embodiments described herein can promote a fast cell growth and a simple economical harvesting method that may be an improvement over existing methods. Example embodiments can include an algal growth system or mechanized harvesting system, which can remove concentrated algae in-situ from an attachment material and can minimize the amount of de-watering needed post-harvest. Example embodiments can optimize gas mass transfer due to the algae cells coming in direct contact with gaseous carbon dioxide when the algae are rotated through the open air. In an alternate embodiment, the algae can be rotated within an enclosed greenhouse 40 (FIGS. 3 and 4) having an increased carbon dioxide concentration relative to the atmosphere, which may improve the growth rate of the algae. Example embodiments can utilize minimal growth medium, where the triangular or vertical design in example embodiments may reduce the total water needed for the growth and the chemical costs of growth medium. In one embodiment, such advantages may be accomplished by submerging only the lowest portion of a bioreactor, supporting material, algal growth system, or mechanized harvesting system into the medium.

Figure 2:
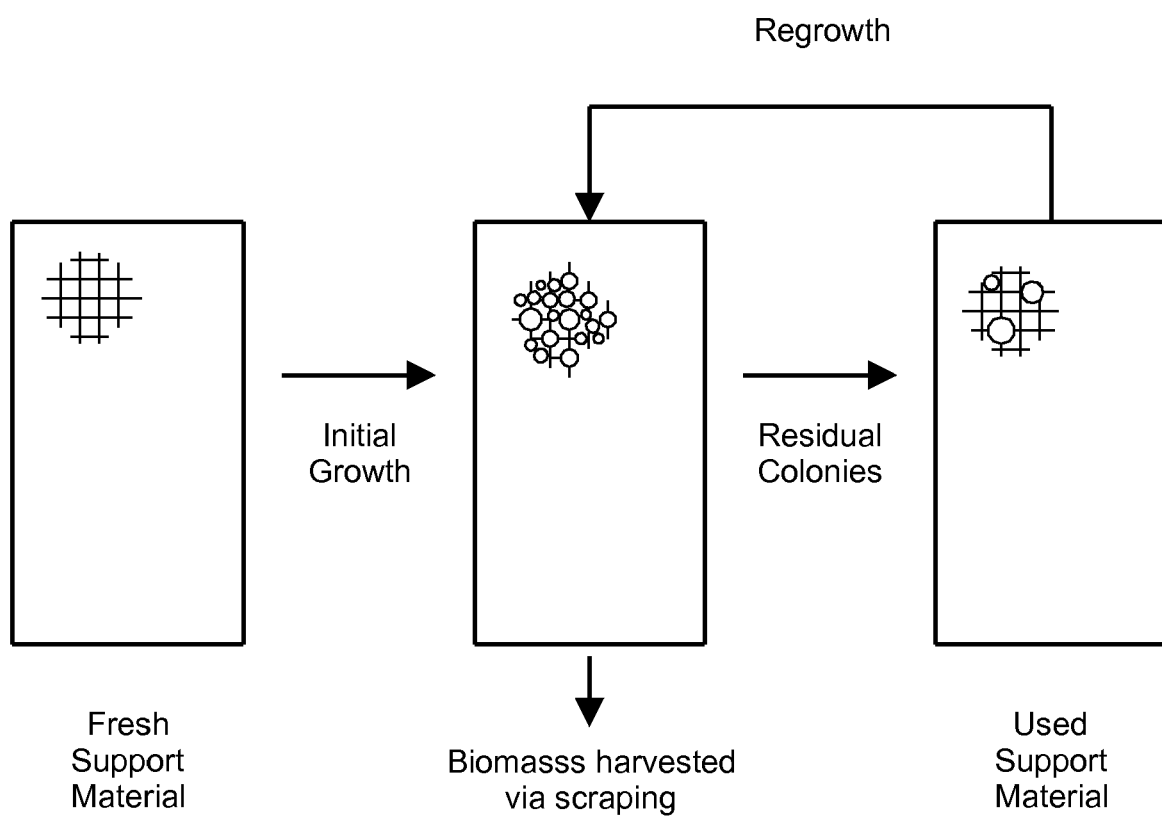
FIG. 2 depicts a top view of microalgae being grown on polystyrene foam.

Referring to FIG. 2, microalgae can be grown on the surface of polystyrene foam. FIG. 2 illustrates how algae can be harvested by scraping the surface of the foam. The mechanical separation through scraping of biomass from the attached materials can result in biomass with water content similar to centrifuged samples (e.g., 80-95% water content) and the residual biomass left on the surface can serve as an ideal inoculum for subsequent growth cycles.

Figure 3:
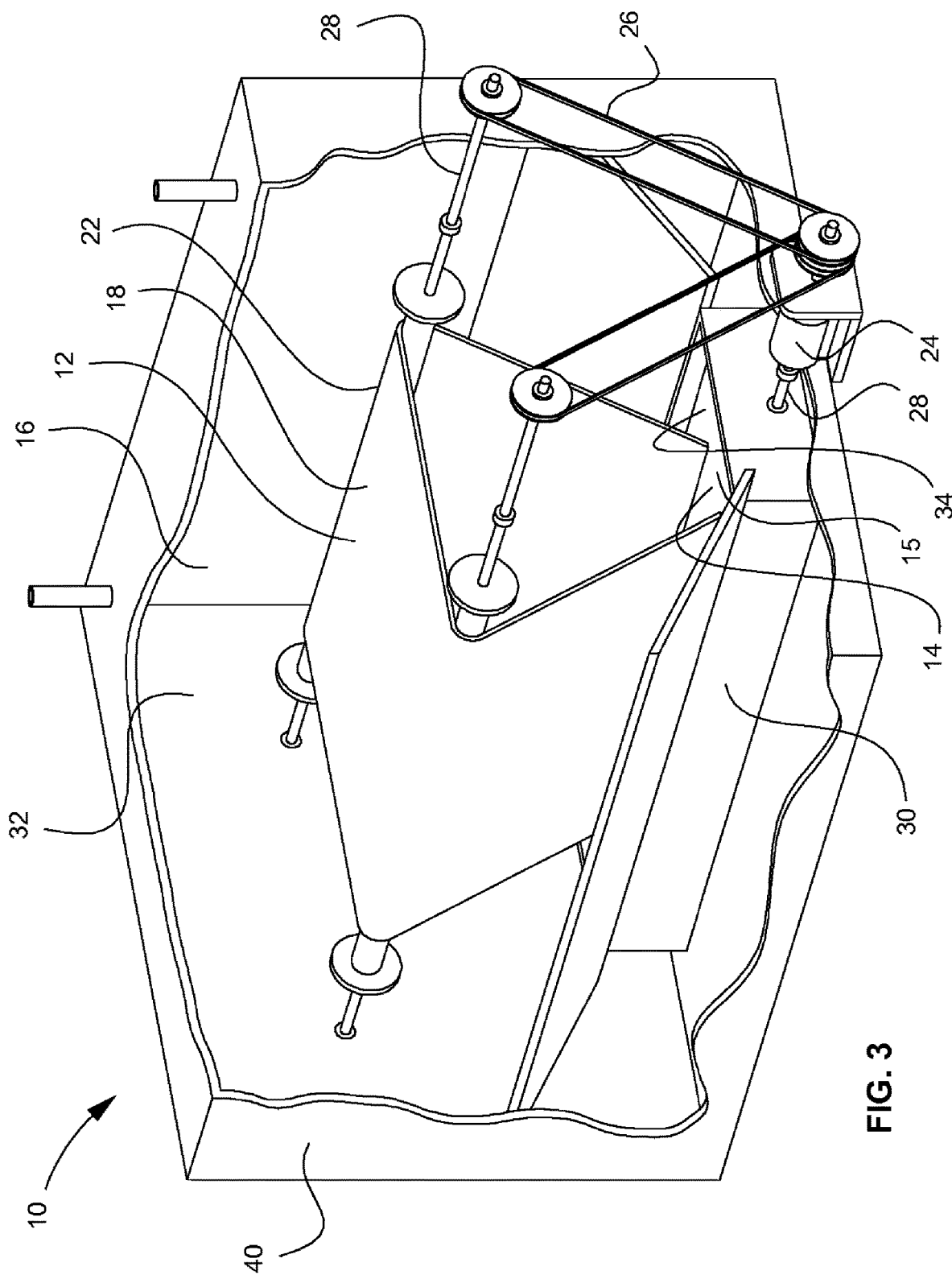
FIG. 3 depicts a partial cutaway perspective view of a revolving algal biofilm photobioreactor according to one embodiment.
Figure 4:
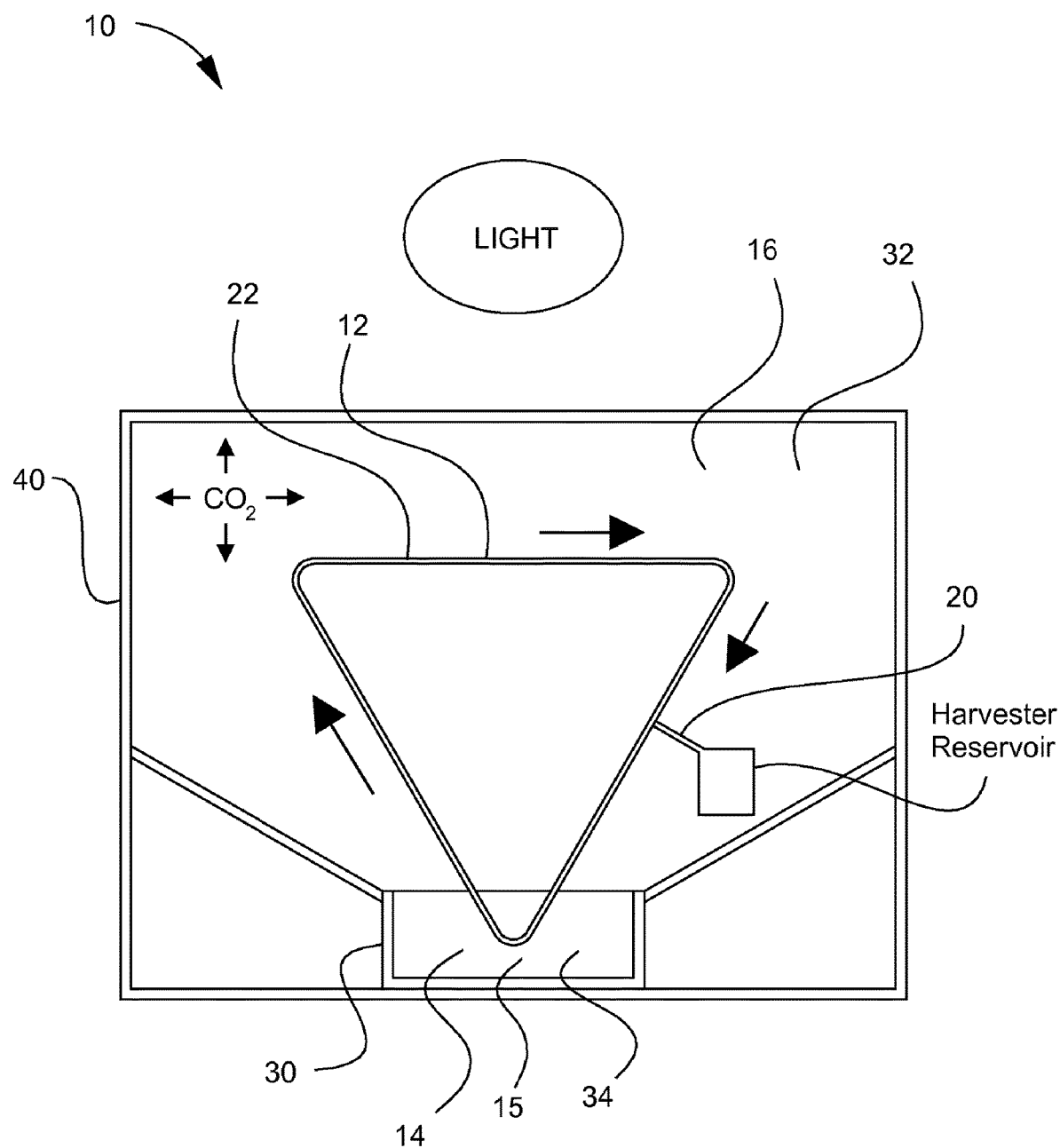
FIG. 4 depicts a schematic front view of the revolving algal biofilm photobioreactor illustrated in FIG. 3.
Figure 7:
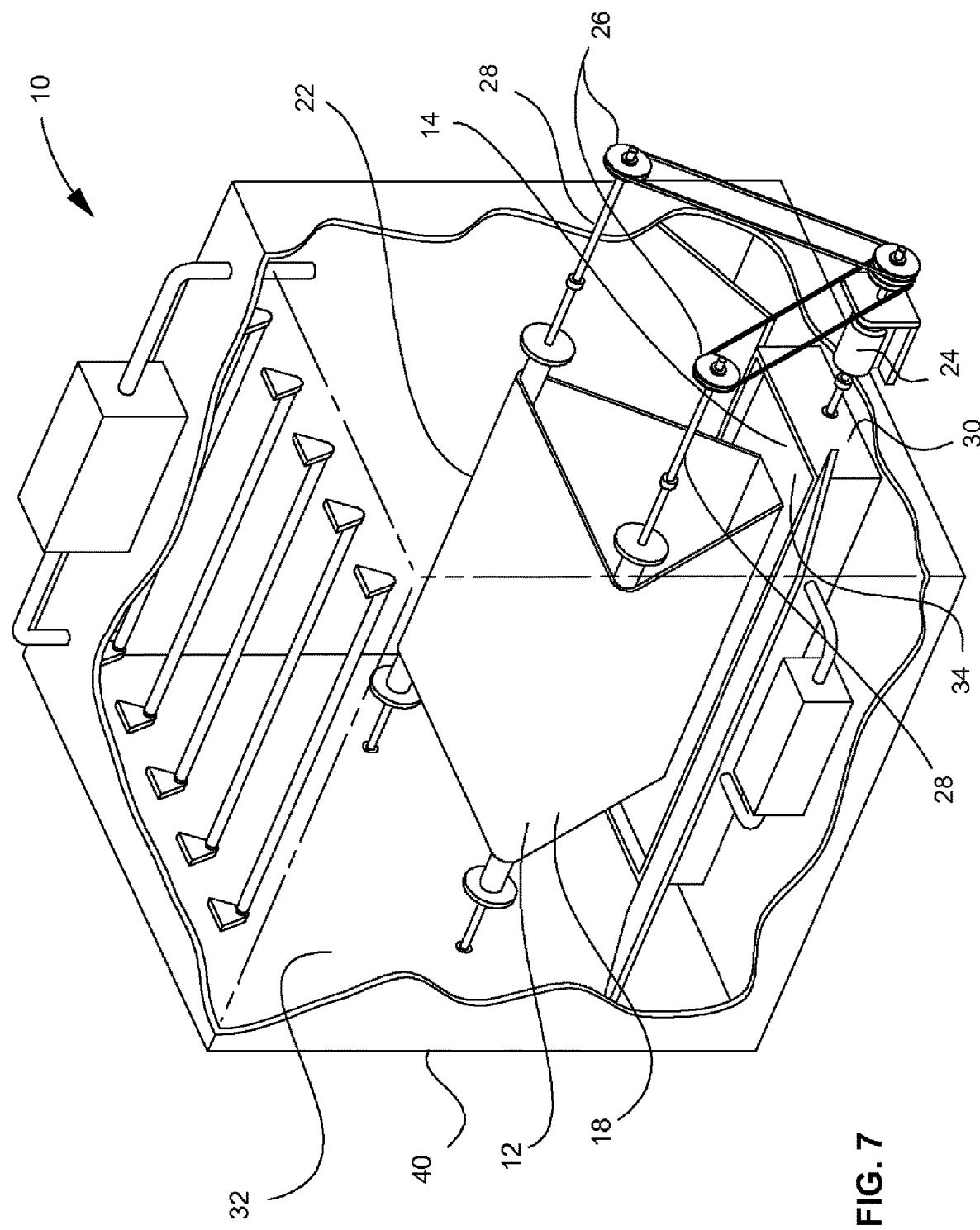
FIG. 7 depicts a partial cutaway perspective view of the revolving algal biofilm bioreactor illustrated in FIG. 3, shown with grow lights and a gas input.

Referring to FIGS. 3, 4, 7, and 8, an example embodiment of a revolving algal biofilm photobioreactor (RAB) 10, in which algal cells 18 can be attached to a solid surface of a supporting material 12, is disclosed. The photobioreactor 10 can keep the algal cells 18 fixed in one place and can bring nutrients to the cells, rather than suspend the algae in a culture medium. As shown in FIGS. 3 and 4, algal cells can be attached to the supporting material 12 that is rotating between a nutrient-rich liquid phase 15 and a CO2-rich gaseous phase 16 for alternative absorption of nutrients and carbon dioxide. The algal biomass can be harvested by scrapping the biomass from the attached surface with a harvesting squeegee 20 (FIG. 4) or other suitable device or system. In example embodiments, the naturally concentrated biofilm can be in-situ harvested during the culture process, rather than using an additional sedimentation or flocculation step for harvesting, for example. The culture can enhance the mass transfer by directly contacting algal cells with CO2 molecules in gaseous phase, where traditional suspended culture systems may have to rely on the diffusion of CO2 molecules from gaseous phase to the liquid phase, which may be limited by low gas-liquid mass transfer rate. Example embodiments may only need a small amount of water by submerging the bottom of the triangle-shaped algal growth system or mechanized harvesting system 22 in contacting liquid 14 while maximizing surface area for algae to attach. Example embodiments can be scaled up to an industrial scale because the system may have a simple structure and can be retrofit on existing raceway pond systems. Example embodiments can be used in fresh water systems and can be adapted to saltwater culture systems. For example, embodiments of this system can be placed in the open ocean instead of in a raceway pond reactor. In this example application, the ocean can naturally supply the algae with sufficient sunlight, nutrient, water, and CO2, which in turn may decrease operational costs. Referring to FIG. 7, a gas input 43 and grow lights 42 having any suitable wavelength can be provided in the system.

Still referring to FIGS. 3, 4, 7, and 8, embodiments of the system can include a drive motor 24 and a gear system 26 that can rotate one or a plurality of drive shafts 28, where the one or a plurality of drive shafts 28 can correspondingly rotate the supporting material 12, such as a flexible sheet material. The supporting material 12 can be rotated into contact with the contacting liquid 14, which can allow the algal cells 18 to attach to the supporting material 12. The drive motor 24 can include a gear system 26 or pulley system that can drive the one or a plurality of drive shafts 28, where the one or a plurality of drive shafts 28 can rotate the supporting material 12 in and out of a contacting liquid 14, for example. Embodiments can also include a liquid reservoir 30, mister, water dripper, or any other suitable component or mechanism that can keep algae, which can be attached to the support material 12, moist. Embodiments can include any suitable scraping system, vacuum system or mechanism for harvesting the algal cells 18 from the supporting material 12. It will be appreciated that the system can include one or a plurality of rollers (not shown) that can be guide and support the supporting material 112 in addition to the one or a plurality of drive shafts 28.

In an example embodiment, a generally triangle-shaped mechanized harvesting system 22 can be provided. Such a configuration can be beneficial in maximizing the amount of sunlight or light that algal cells 18 are exposed to. However versions of the system can be designed, for example, in any configuration that includes a "sunlight capture" part 32 which can be exposed to air and sunlight, and a "nutrient capture" part 34 which can be submerged into a nutrient solution or contacting liquid 14. It will be appreciated that, in a first position, the supporting material 12 can have a portion that is in the "sunlight capture" part 32 and a portion that is in the "nutrient capture" part 34, where rotation of the supporting material 12 to a second position can result in different regions corresponding to the "sunlight capture" part 32 and "nutrient capture" part 34. Such movement of the supporting material 12 can, for example, beneficially transition algal cells 18 from a nutrient rich liquid to a region with sunlight and a carbon dioxide content higher than the outside atmosphere. As will be shown in more detail herein, a substantially vertical design is contemplated, which may be the simplest and most cost efficient design because such a system may minimize the amount of wasted space and may maximize the amount of algae produced in a small area by growing this system vertically. Alternative designs can include a straight vertical reactor, a reactor that is straight but slightly angled to provide more surface area for sunlight to hit, a cylindrical reactor, or a square shaped reactor.

Figure 8:
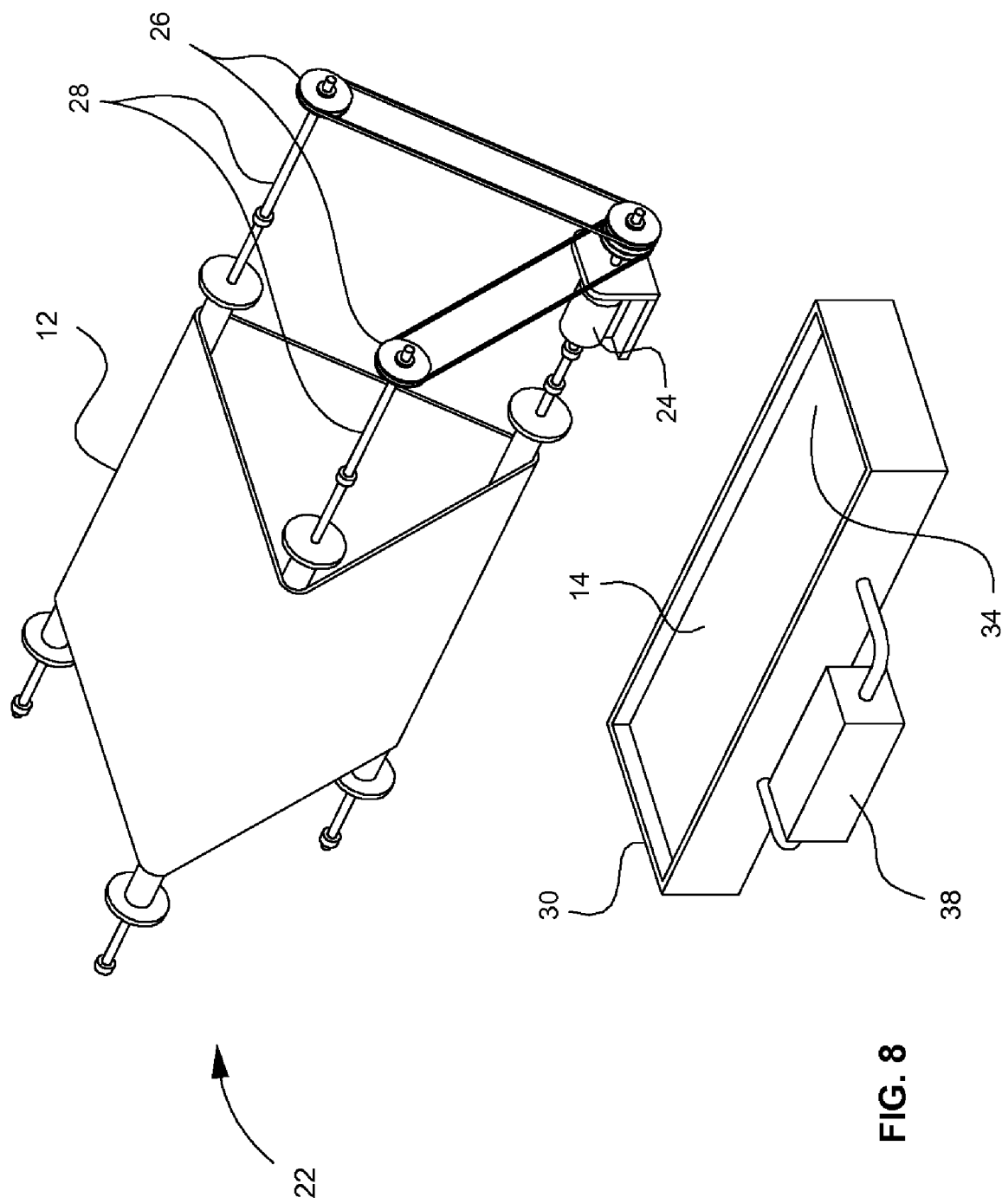
FIG. 8 depicts a partial exploded view of the revolving algal biofilm bioreactor shown in FIG. 3.

Referring to FIG. 8, the generally triangle-shaped algal growth and mechanized harvesting system 22 can include a supporting material 12 that is movable or removable relative to the liquid reservoir 30. The supporting material 12, and any associated components such as the one or a plurality of drive shafts 28 and gear system 26, can be movable or removable for cleaning, replacement, harvesting, adjustment, or the like. It will be appreciated that such movement can be manual or can be automated if desirable. In an example embodiment, the liquid reservoir 30 can contain a contacting liquid 14 having a first chemical or fluid makeup, where the supporting material 12 can be lifted or otherwise transitioned from the liquid reservoir 30 into a second liquid reservoir (not shown) having a second liquid (not shown) having a different chemical or fluid makeup from the contacting liquid 14. In this manner, the supporting material 12 retaining algal cells 18 can be dipped or transitioned into a variety of fluids or materials that may maximize algal growth or otherwise provide a benefit. Such a system can be repeated or adjusted as appropriate. In an alternate embodiment, the supporting material can be lifted or moved from the liquid reservoir 30 and transitioned to a harvesting station. In one embodiment, harvesting can take place while the supporting material 12 is positioned within the liquid reservoir 30.

Still referring to FIG. 8, the liquid reservoir 30 can include a pump 38 or any other suitable actuator or fluid control. The pump 38 can circulate the contacting liquid 14, which may improve the growth of algal cells 18 and the efficiency of the overall system. It will be appreciated that the pump 38 can be an electric pump, a wheel, a paddlewheel, or can have any other suitable configuration to create any desirable flow pattern. It will be appreciated that the pump 38 can heat, cool, or otherwise adjust the conditions associated with the contacting liquid 14. The pump 38 can also be configured for the delivery of supplemental nutrients, such as supplemental fluids delivered at pre-specified times, where such delivery can be manual or automated. It will be appreciated that the pump 38, and any other suitable components, can be associated with a computer, controller, or microcontroller that can be programmed to provide any suitable automated functionality.

Figure 5:
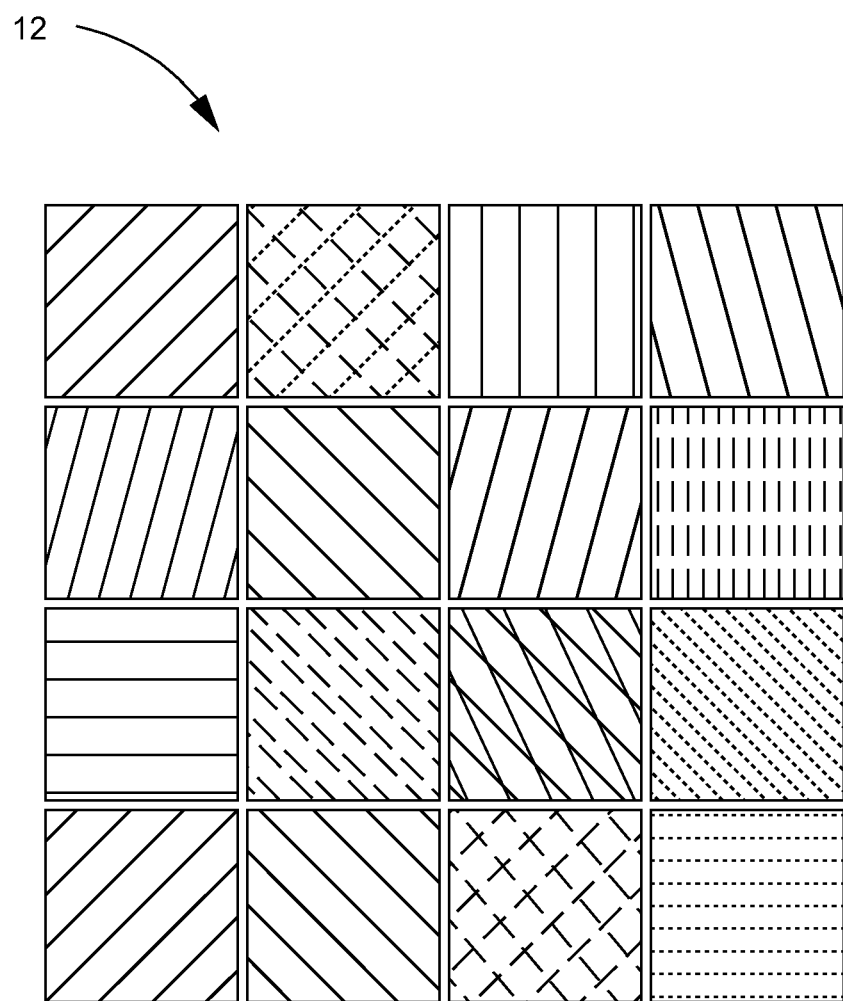
FIG. 5 depicts a top view of microalgae being grown on a variety of materials.

Referring to FIG. 5, any suitable supporting material 12, such as any suitable flexible fabric, can be used with the systems and methods described herein to grow any suitable material. For example, the microalga *Chlorella*, such as *Chlorella vulgaris* can be grown on materials such as, muslin cheesecloth, aramid fiberglass, porous PTFE coated fiberglass, chamois, vermiculite, microfiber, synthetic chamois, fiberglass, burlap, cotton duct, velvet, TYVEK, polylactic acid, abrased poly-lactic acid, vinyl laminated nylon, polyester, wool, acrylic, lanolin, woolen, cashmere, leather, silk, lyocell, hemp fabric, SPANDEX, polyurethane, olefin fiber, polylactide, LUREX, carbon fiber, and combinations thereof. The supporting material or associated material can include rubbers such as, for example, buna-n Rubber, butyl rubber, ECH rubber, EPDM rubber, gum rubber, polyethylene rubber, latex rubber, neoprene rubber, polyurethane, santoprene rubber, SBR rubber, silicone rubber, vinyl rubber, VITON fluoroelastomer, aflas, fuorosilicone, or combinations thereof. The supporting material or associated material can include plastics such as, for example, PETG, acrylic, cast acrylic, cellulose, polycarbonate, LDPE, PLA, PVC, ABS, polystyrene, HDPE, polypropylene, UHMW, delrin, acetal resin, nylon, cast nylon, CPVC, rexolite polystyrene, noryl PPO, polyester, PVDF, polysulfone, radel PPSU, ulrem PEI, FEP, PPS, PEEK, PFA, torlon PAI, reflon PTFE, polyimide, antistatic polycarbonate, antistatic cast acrylic, conductive ABS/PVC, antistatic acetal, atatic-dissipative UHMW, conductive UHMW, antistatic PTFE, glass-filled polycarbonate, strengthened acrylic, strengthened PVC, glass-filled nylon, glass-Filled acetal, glass-filled UHMW, glass-filled PTFE, and combinations thereof. The supporting material and associated materials can include metals such as, for example, aluminum, steel, cast iron, tungsten carbide, tungsten alloy, stainless steel, nickel, titanium, copper, brass, bronze, lead, tin, zinc, casting alloys, or combinations thereof. Any suitable material for the supporting material and associated materials is contemplated including ceramic, felt, fiberglass, foam, foam rubber, foam plastic, glass, leathers, carbon fiber, wire cloth, or the like.

Figure 18:
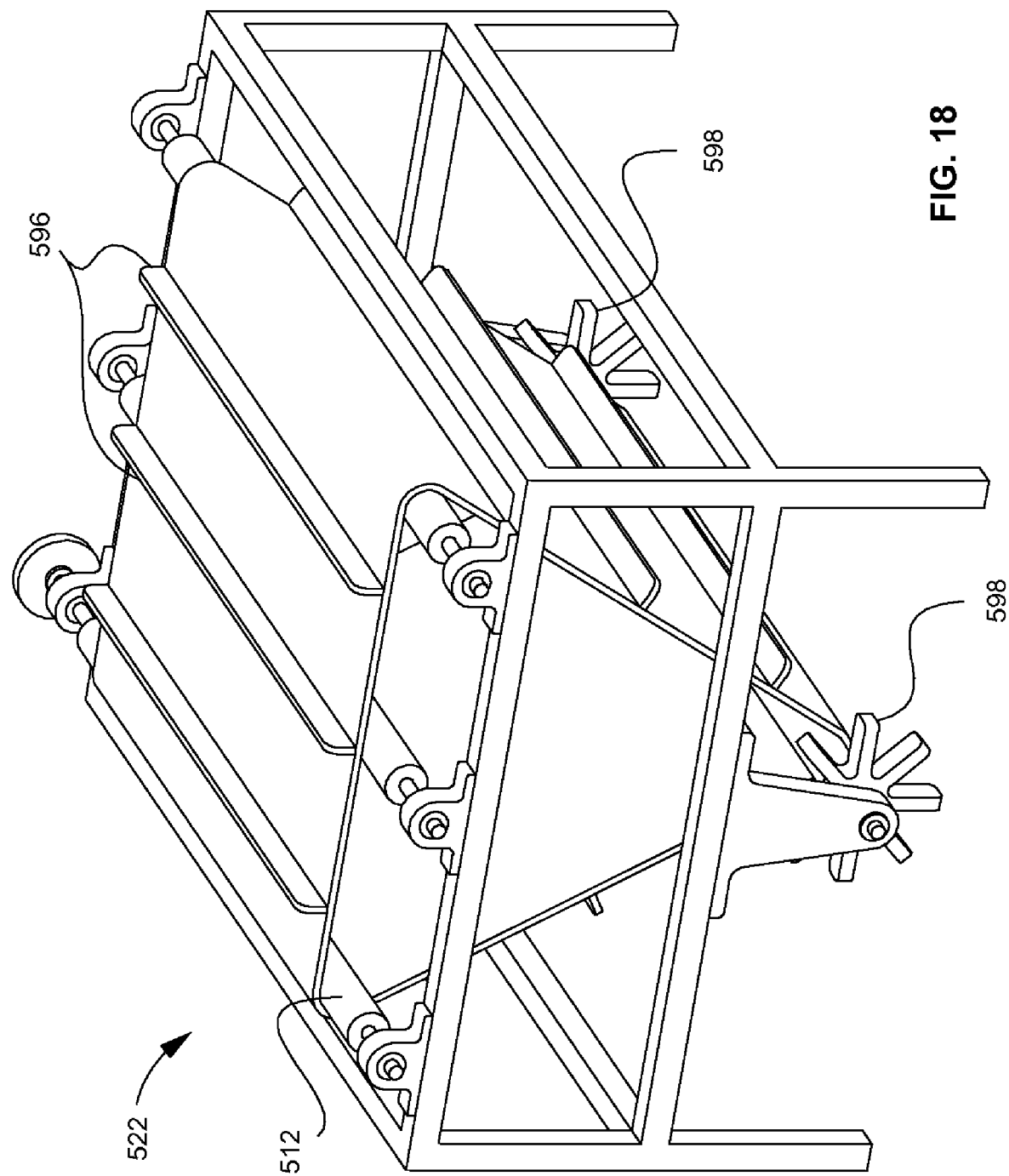
FIG. 18 depicts a perspective view of an algal growth system according to one embodiment.

The material associated with the supporting material 12 can have a high surface roughness, high hydrophobicity, and high positive surface charge in one embodiment. It will be appreciated that any suitable texture, surface treatment, hybrid material, or the like is contemplated. The supporting material, belt, sheet, or band can be altered, modified, or changed with heat, abrasion, applying another material, chemically treating, applying a charged molecule, applying a polar molecule, or combinations thereof. Referring to FIG. 18, in one embodiment of an algal growth system 522, the supporting material 512 can including one or a plurality of ribs 596, can be finned, or otherwise textured such that a pump is not needed to agitate an associated contacting liquid, where rotation of the textured supporting material can sufficiently agitate or otherwise create a desirable fluid dynamic. The algal growth system 522 can also include an integrated paddle 598 that can be positioned within a contacting liquid such that rotation of the supporting material 512 correspondingly can rotate the integrated paddle 598. In alternate embodiments, the supporting material can include flexible regions and rigid regions, can be a hinged belt, can have removable sections, or can otherwise be suitably configured. For example, in one embodiment, strips of material can be attached to a rotating belt with a hook and loop fastener, where such strips can be pulled off of the rotating belt during harvesting and replaced when harvesting is complete.

The supporting material 12 can be reinforced by attaching a high strength and slowly degradable second layer of material to a cell growth material. The photobioreactor 10 can be configured such that the high strength material comes in contact with components such as rollers, drive shafts, and the like. Such a configuration may help avoid the wearing off of the cell growth material during operation of the photobioreactor 10. Suitable materials can include materials that are not easily degraded by water and microbes such as plastic, rubber, TYVEK, or other slowly degrading materials. Additionally, materials, adhesives, chemicals, or the like can be sprayed onto or otherwise provided on the supporting material 12 to facilitate algal attachment. It will be appreciated that any suitable number of layers of material is contemplated.

It will be appreciated that any suitable algal cells 18 (including cyanobacteria) as well as fungal strains, such as strains that can be used in aquaculture feed, animal feed, nutraceuticals, or biofuel production can be used. Such strains can include *Nannochloropsis* sp., which can be used for both biofuel production and aquacultural feed, *Scenedesmus* sp., a green microalga that can be used in wastewater treatment as well as for fuel production feedstock, Haematococcus sp, which can produce a high level of astaxanthin, *Botryococcus* sp. a green microalga with high oil content, *Spirulina* sp. a blue-green alga with high protein content, *Dunaliella* sp. a green microalga containing a large amount of carotenoids, and/or a group of microalgae species producing a high level of long chain polyunsaturated fatty acids can include Arthrospira, Porphyridium, *Phaeodactylum, Nitzschia, Crypthecodinium* and Schizochytrium. Any suitable parameter, including gaseous phase CO2 concentration, harvesting frequency, the rotation speed of the RAB reactor, the depth of the biofilm harvested, the ratio of submerged portion to the air-exposure portion of the RAB reactor, or the gap between the different modules of the RAB system can be optimized for any suitable species. It will be appreciated that the listed genus and species are described by way of example and additions and combinations are contemplated.

Figure 6:
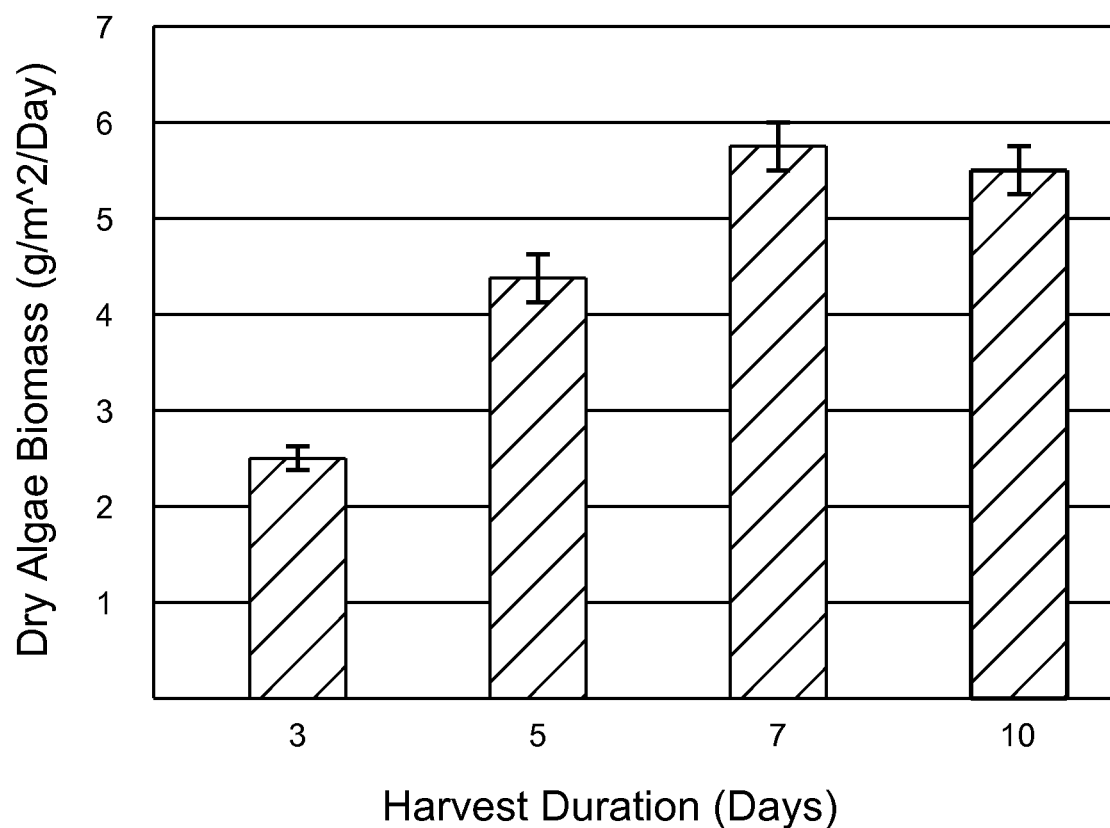
FIG. 6 depicts a bar chart of harvesting frequencies for an algal strain according to one embodiment.

Referring to FIG. 6, any harvesting schedule can be used in accordance with example embodiments described herein. The mechanism of harvesting biomass from the biofilm can be, for example, scraping, high pressure air, vacuum, or combinations thereof. Biomass productivity may vary by species and any suitable harvesting time is contemplated to maximize such productivity. For example, as shown in FIG. 6, of this specific species as a function of harvesting time by growing the algae on a RAB system then harvesting the cells at different durations. As shown in FIG. 6, for *Chlorella* the optimal harvest frequency may be every 7 days. In example embodiments, managing other parameters such as CO2 concentration and nutrient loading may also impact algal growth performance.

Figure 9:
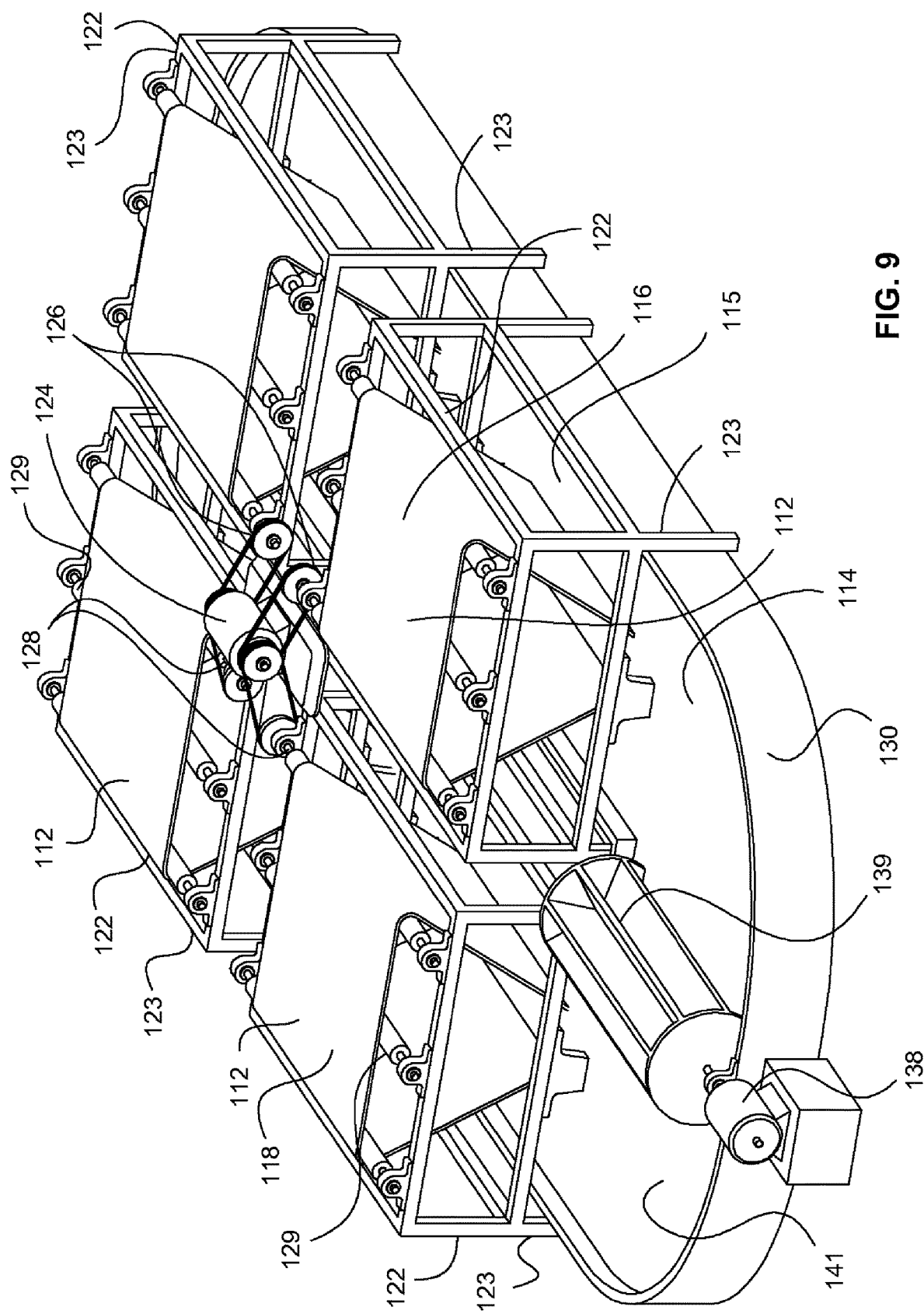
FIG. 9 depicts a perspective view of a revolving algal biofilm bioreactor having a plurality of associated algal growth systems and a raceway according to one embodiment.
Figure 10:
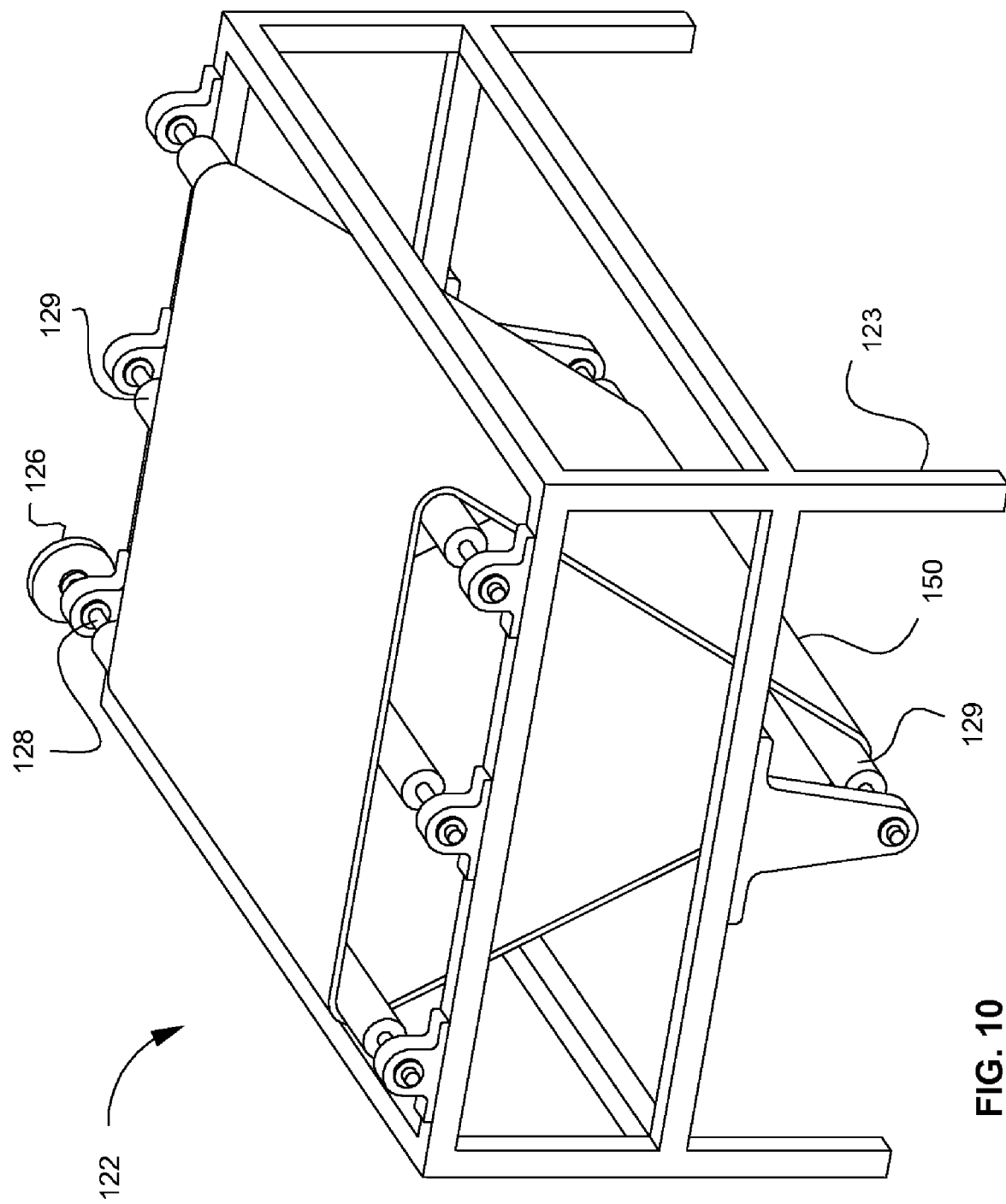
FIG. 10 depicts a perspective view of the algal growth system illustrated in FIG. 12.
Figure 11:
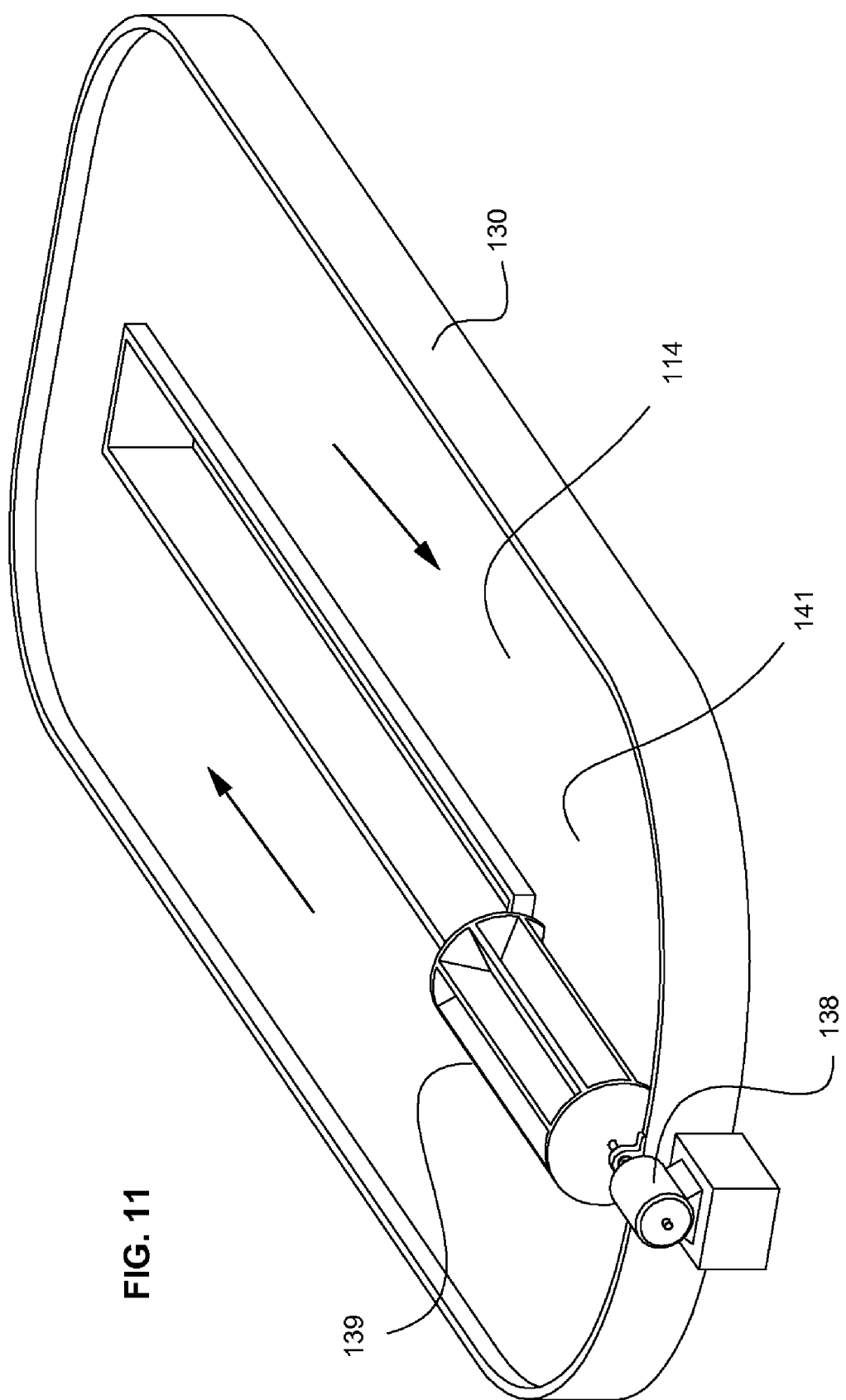
FIG. 11 depicts a perspective view of the raceway illustrated in FIG. 12.

Referring to FIGS. 9-11, shown is an alternate embodiment of a revolving algal biofilm photobioreactor (RABP) 100, in which algal cells 118 can be attached to a solid surface of a supporting material 112 that can be rotated between a nutrient-rich liquid phase 115 and a CO2-rich gaseous phase 116 for alternative absorption of nutrients and carbon dioxide. The algal biomass can be harvested by scrapping the biomass from the attached surface with a harvesting mechanism (not shown) such as a squeegee, vacuum, reaper, or the like. The photobioreactor 100 may require only a small amount of water for operation, relative to existing methods, where only the bottom 150 (FIG. 10) of an algal growth unit or mechanized harvesting unit 122 may be immersed in a contacting liquid 114. The photobioreactor 100 can include one or a plurality of mechanized harvesting units 122, having frames 123, that can be positioned in a raceway 130 containing contacting fluid 114. Example embodiments can include a large number of mechanized harvesting units such that the photobioreactor can be scaled up to an industrial scale. For example, a single raceway could have 20, 50, 100, or more mechanized harvesting units. In an example embodiment, the one or a plurality of mechanized harvesting units 122 can be retrofitted onto existing raceway pond systems. Example embodiments can be used in fresh water systems and can be also be adapted to saltwater culture systems. In one example, the ocean can naturally supply the algal cells with sufficient sunlight, nutrient, water, and CO2, which in turn may decrease operational costs associated with operation of a photobioreactor. Embodiments of the mechanized harvesting units can be placed, for example, in any suitable fluid retaining location or device.

Embodiments of the photobioreactor 100 can include a drive motor 124 and a gear system 126 that can rotate one or a plurality of drive shafts 128, where the one or a plurality of drive shafts 128 can correspondingly rotate the supporting material 112, such as a flexible sheet material for growing algal cells 118. The photobioreactor 100 can include one or a plurality of rollers 129 that can support and guide the supporting material 112. The supporting material 112 can be rotated into contact with the contacting liquid 114, which can allow the algal cells 118 to attach to the supporting material 112. The drive motor 124 can include a gear system 126 or pulley system that can drive the one or a plurality of drive shafts 128, where the one or a plurality of drive shafts 128 can rotate the supporting material 112 into and out of the contacting liquid 114. Embodiments can also include a raceway 130, mister, water dripper, or any other suitable component or mechanism that can keep algae, which can be attached to the support material 112, moist. Embodiments can include any suitable scraping system, vacuum system or mechanism for harvesting the algal cells 118 from the supporting material 112. It will be appreciated that the drive motor 124 can be associated with a plurality of mechanized harvesting units 122 or, in an alternate embodiment, each mechanized harvesting unit can be associated with an independent motor, gear, and/or drive shaft system. It may be efficient to operate one or more of the mechanized harvesting units on the same schedule, but it may also be advantageous to operate some or all of the mechanized harvesting units on different schedules. For example, in one embodiment, a mechanized harvesting unit exposed to natural light can be associated with a light sensor (not shown) and controller (not shown) such that the rotation speed of the supporting material is optimized relative to the available light. In such an example, mechanized harvesting units in the same facility may have different, or slightly different environmental conditions, where operating each mechanized harvesting unit independently may substantially optimize the overall system.

The mechanized harvesting unit 122 can have a generally triangle-shaped configuration supported by the frame 123. It will be appreciated that the frame 123 can be constructed from any suitable material, such as metal, and can have any suitable configuration. The frame 123 can be substantially level relative to a flat surface, can be stepped, or otherwise shaped to accommodate an incline or an uneven surface. The frame 123 can include telescoping components (not shown), such as telescoping legs, which may allow the frame to be used effectively as a retrofit in existing raceways, for example. The frame 123 can be stackable (not shown) or can be coupled in a side-by-side fashion with other frames in an interlocking manner such that a plurality of mechanized harvesting systems can be connected to form a photobioreactor. Such a modular system may allow for a few mechanized harvesting system designs to be used in a wide variety of locations and situations.

One or a plurality of mechanized harvesting units 122 can be associated with the raceway 130 in any suitable manner or configuration. For example, each mechanized harvesting unit 122 can be integral with or permanently affixed to the raceway 130. In an alternate embodiment, each mechanized harvesting unit 122 can be selectively removable or adjustable relative to the raceway 130, where the mechanized harvesting unit 122 can be removed for cleaning, harvesting, replacement, upgrade, or the like.

Referring to FIG. 11, the raceway 130 can have any suitable shape or configuration. In one example, the raceway 130 can include a motor 138 that can be configured to drive a paddlewheel 139. The paddlewheel 139 can be configured to create a current or flow within the raceway 130 that may facilitate the growth of algal cells 118. It will be appreciated that the raceway, motor, and paddlewheel are shown by way of example only, where any suitable mechanism to provide a desirable flow or current in a suitable reservoir is contemplated. The raceway 130 can be open or otherwise exposed to light such that algae can easily grow within the raceway 130. The raceway 130 can have a region 141 that can be exposed to light and may not contain a mechanized harvesting unit, where the region 141 can be used to cultivate or grow a supply of algal cells 118 within the raceway 130. Providing such a region 141, where the region 141 can have any suitable shape or configuration, may make the system self-sustaining and may reduce the likelihood that the system needs to be seeded or re-seeded with algal cells.

Figure 12:
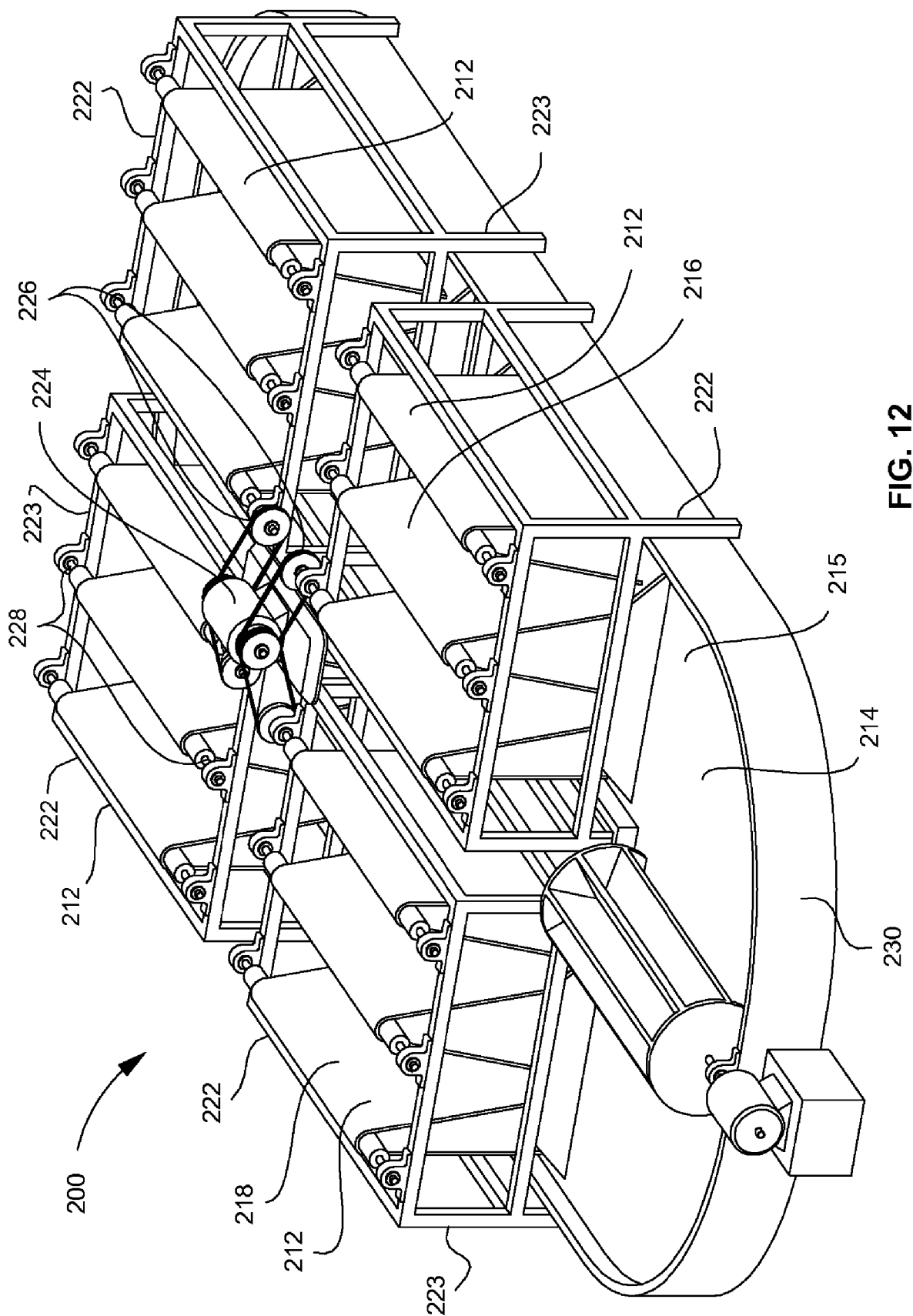
FIG. 12 depicts a perspective view of a revolving algal biofilm bioreactor having a plurality of associated algal growth systems and a raceway according to an alternate embodiment.
Figure 13:
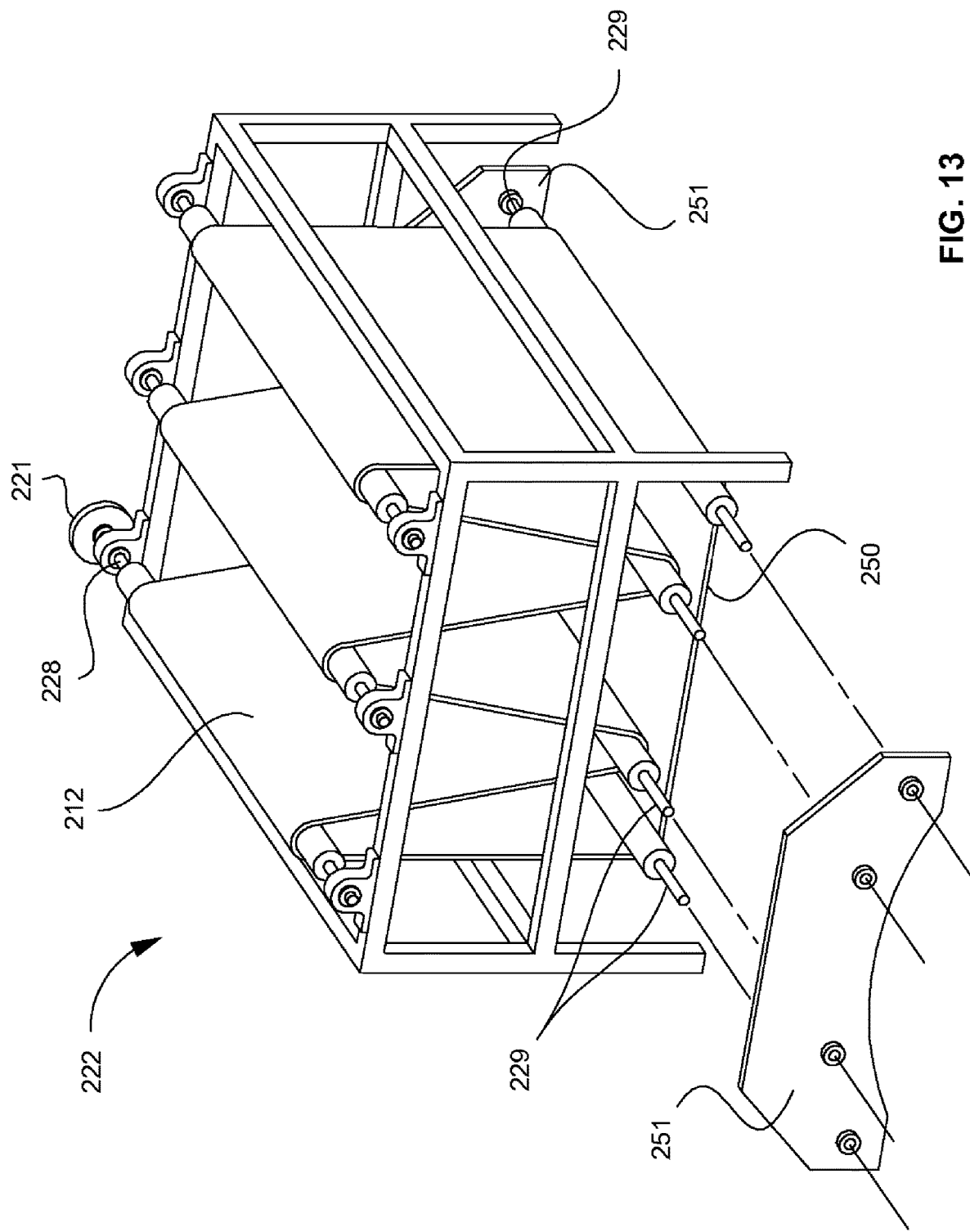
FIG. 13 depicts a perspective view of the algal growth system illustrated in FIG. 12.

Referring to FIGS. 12 and 13, shown is an alternate embodiment of a revolving algal biofilm photobioreactor (RAB) 200, in which algal cells 218 can be attached to a solid surface of a supporting material 212 that can be rotated between a nutrient-rich liquid phase 215 and a CO2-rich gaseous phase 216 for alternative absorption of nutrients and carbon dioxide. The algal biomass can be harvested by scrapping the biomass from the attached surface with a harvesting mechanism (not shown) such as a squeegee, vacuum, reaper, or the like. The photobioreactor 200 may require only a small amount of water for operation, relative to existing methods, where only the bottom 250 (FIG. 13) of an algal growth unit or mechanized harvesting unit 222 may be immersed in a contacting liquid 214. The photobioreactor 200 can include one or a plurality of mechanized harvesting units 222, having frames 223, which can be positioned in a raceway 230 containing contacting fluid 214. Example embodiments can include a large number of mechanized harvesting units such that the photobioreactor can be scaled up to an industrial scale. For example, a single raceway could have 20, 50, 100, or more mechanized harvesting units. In an example embodiment, the one or a plurality of mechanized harvesting units 222 can be retrofitted onto existing raceway pond systems. Embodiments of the mechanized harvesting units can be placed, for example, in any suitable fluid retaining location or device.

Embodiments of the photobioreactor 200 can include a drive motor 224 and a gear system 226 that can rotate one or a plurality of drive shafts 228, where the one or a plurality of drive shafts 228 can correspondingly rotate the supporting material 212, such as a flexible sheet material for growing algal cells 218. The photobioreactor 200 can include one or a plurality of rollers 229 that can support and guide the supporting material 112. The supporting material 212 can be rotated into contact with the contacting liquid 214, which can allow the algal cells 218 to attach to the supporting material 212. The drive motor 224 can include a gear system 226 or pulley system that can drive the one or a plurality of drive shafts 228, where the one or a plurality of drive shafts 228 can rotate the supporting material 212 into and out of the contacting liquid 214. Embodiments can also include a raceway 230, mister, water dripper, or any other suitable component or mechanism that can keep algae, which can be attached to the support material 212, moist. Embodiments can include any suitable scraping system, vacuum system or mechanism for harvesting the algal cells 218 from the supporting material 212. It will be appreciated that the drive motor 224 can be associated with a plurality of mechanized harvesting units 222 or, in an alternate embodiment, each mechanized harvesting unit can be associated with an independent motor, gear, and/or drive shaft system. It may be efficient to operate one or more of the mechanized harvesting units on the same schedule, but it may also be advantageous to operate some or all of the mechanized harvesting units on different schedules. For example, in one embodiment, a mechanized harvesting unit exposed to natural light can be associated with a light sensor (not shown) and controller (not shown) such that the rotation speed of the supporting material is optimized relative to the available light. In such an example, mechanized harvesting units in the same facility may have different, or slightly different environmental conditions, where operating each mechanized harvesting unit independently may substantially optimize the overall system.

The mechanized harvesting unit 222 can have a generally wave-shaped configuration supported by the frame 223. It will be appreciated that the frame 223 can be constructed from any suitable material, such as metal, and can have any suitable configuration in accordance with embodiments described herein. The supporting material 212 of the mechanized harvesting unit can have a substantially wave-shaped configuration as best illustrated in FIG. 13. The supporting material 212 can be a contiguous band of material and can be wound about the one or a plurality of drive shafts 228 or rollers 229 such that any suitable configuration is created. It is contemplated that the supporting material can be a long, contiguous band of material having multiple peaks and valley, as illustrated in FIG. 12. As illustrated, a portion of the supporting material 212 can also pass along the bottom 250 of the mechanized harvesting unit 222. It will be appreciated that a single long band and a plurality of bands having any suitable relationship or configuration are contemplated. In an example embodiment, the one or a plurality of drive shafts 228 or rollers 229 can be adjusted such that different configuration can be created using the same frame 223. Such an interchangeable system may be beneficial in that certain configurations may be beneficial to particular species of algal cells. An interchangeable system may also allow for different environmental conditions, uses, or use on a wide range of scales. Any other suitable component, such as a plate 251 can be provided to secure components, such as the rollers 229, in a desired configuration.

Figure 14:
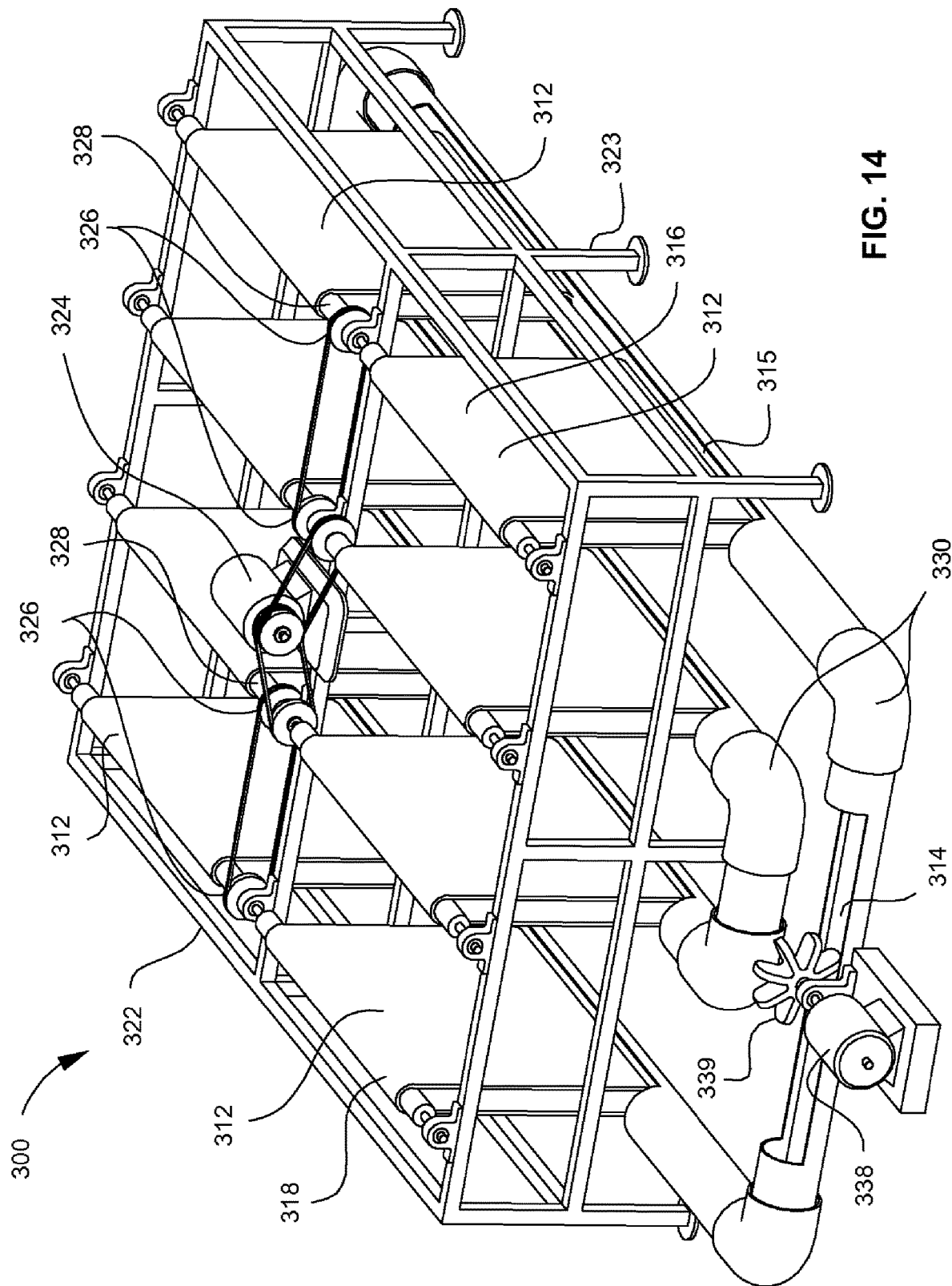
FIG. 14 depicts a perspective view of a revolving algal biofilm bioreactor having an associated algal growth system and a trough system according to one embodiment.
Figure 15:
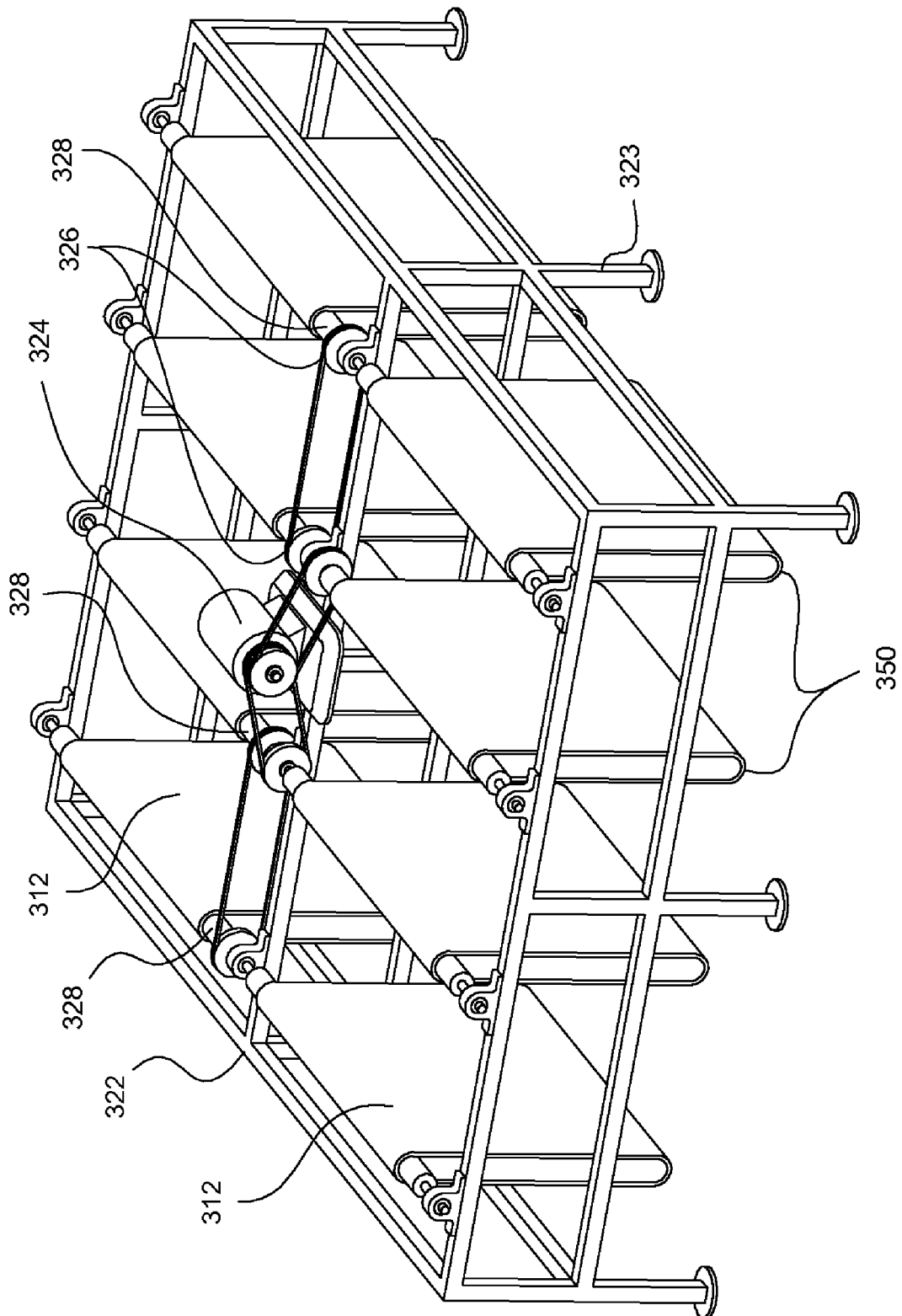
FIG. 15 depicts a perspective view of the algal growth system illustrated in FIG. 14.
Figure 16:
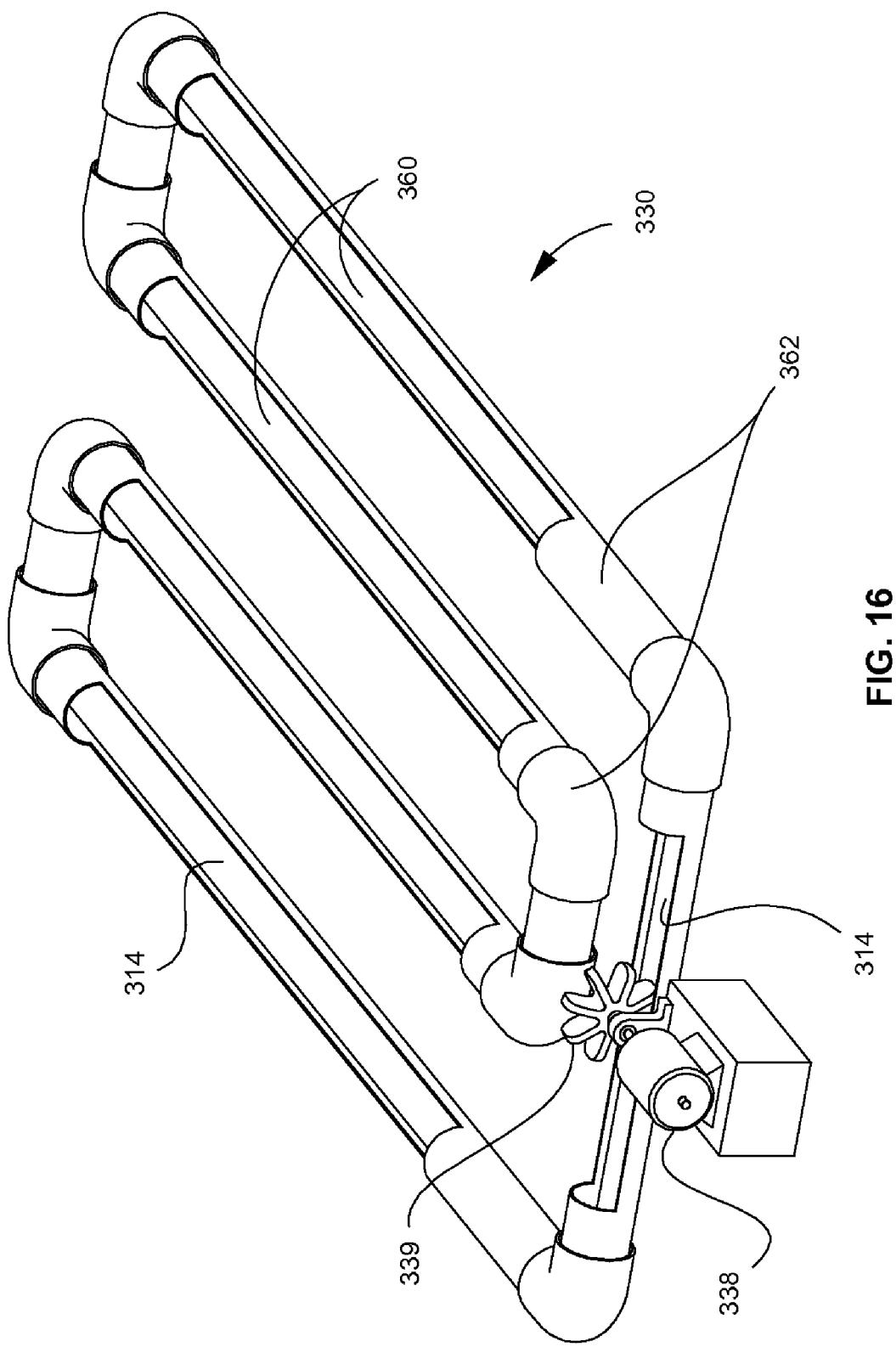
FIG. 16 depicts a perspective view of the trough system illustrated in FIG. 14.

Referring to FIGS. 14-16, shown is an alternate embodiment of a revolving algal biofilm photobioreactor (RAB) 300, in which algal cells 318 can be attached to a solid surface of one or a plurality of supporting materials 312 that can be rotated between a nutrient-rich liquid phase 315 and a CO2-rich gaseous phase 316 for alternative absorption of nutrients and carbon dioxide. The algal biomass can be harvested by scrapping the biomass from the attached surface with a harvesting mechanism (not shown) such as a squeegee, vacuum, reaper, or the like. The photobioreactor 300 may require only a small amount of water for operation, relative to existing methods, where only the bottom 350 (FIG. 15) of an algal growth unit or mechanized harvesting unit 322 may be immersed in a contacting liquid 314. The photobioreactor 300 can include a frame 323, which can be positioned in a trough system 330 containing contacting fluid 314. Example embodiments can include a large number of mechanized harvesting units such that the photobioreactor can be scaled up to an industrial scale. For example, a single trough system could have 20, 50, 100, or more mechanized harvesting units or independent supporting material units. In an example embodiment, the one or a plurality of mechanized harvesting units 322 can be retrofitted onto existing raceway pond systems. Embodiments of the mechanized harvesting units can be placed, for example, in any suitable fluid retaining location or device.

It will be appreciated that the trough system 330 is show by way of example only, where any suitable tubing, configuration, or construction is contemplated. The trough system 330 can have a serpentine configuration such that the trough system 330 forms a substantially closed circuit for fluid flow. The trough system 330 can have any suitable shape, where the trough system 330 can have interchangeable parts such that different configurations can be created by a user. The trough system can include any suitable number of apertures 360 and closed sections 362, where apertures 360 can be configured to accept each of the one or a plurality of supporting materials 312. In one embodiment, the apertures 360 can be associated with a closure when not in use. Alternatively, apertures 360 can be used in sunlight or well lighted areas to help facilitate algal growth in the contacting liquid 314. The trough system 330 can be associated with a motor 338 and paddlewheel 339 that can be configured to create a fluid dynamic or current flow in the trough system 330. In one embodiment, one or a plurality of paddlewheels 339, or other actuators, can be positioned in the apertures 360.

Embodiments of the photobioreactor 300 can include a drive motor 324 and a gear system 326 that can rotate one or a plurality of drive shafts 328, where the one or a plurality of drive shafts 328 can correspondingly rotate the one or a plurality of supporting materials 312, such as a flexible sheet material for growing algal cells 318. The photobioreactor 300 can include one or a plurality of rollers that can support and guide the one or a plurality of supporting materials 312 or, as illustrated in FIG. 15, the bottom of each of the one or a plurality of supporting materials 312 can hang freely in a substantially vertical configuration. The one or a plurality of supporting materials 312 can be rotated into contact with the contacting liquid 314, which can allow the algal cells 318 to attach to the one or a plurality of supporting materials 312. The drive motor 324 can include a gear system 326 or pulley system that can drive the one or a plurality of drive shafts 328, where the one or a plurality of drive shafts 328 can rotate the one or a plurality of supporting materials 312 into and out of the contacting liquid 314. Embodiments can also include a trough system 330, mister, water dripper, or any other suitable component or mechanism that can keep algae, which can be attached to the one or a plurality of supporting materials 312, moist. Embodiments can include any suitable scraping system, vacuum system or mechanism for harvesting the algal cells 318 from the one or a plurality of supporting materials 312. It will be appreciated that the drive motor 324 can be associated with a plurality of mechanized harvesting units 322 or one or a plurality of supporting materials 312. In an alternate embodiment, each of the one or a plurality of supporting materials 312 can be associated with an independent motor, gear, and/or drive shaft system (not shown). It may be efficient to operate one or more of the one or a plurality of supporting materials 312 on the same schedule, but it may also be advantageous to operate some or all of the one or a plurality of supporting materials 312 on different schedules. For example, in one embodiment, a supporting material exposed to natural light can be associated with a light sensor (not shown) and controller (not shown) such that the rotation speed of the supporting material is optimized relative to the available light. In such an example, one or a plurality of supporting materials in the same facility may have different, or slightly different environmental conditions, where operating each one or a plurality of supporting materials independently may substantially optimize the overall system.

The mechanized harvesting unit 322 can have a generally vertically-shaped configuration of one or a plurality of supporting materials 312 that can be supported by the frame 323. It will be appreciated that the frame 323 can be constructed from any suitable material, such as metal, and can have any suitable configuration in accordance with embodiments described herein. Each of the one or a plurality of supporting materials 312 can be a contiguous band of material, strips, ropes, slats, ribbons, plates, scales, overlapping material, or the like, and can be wound about the one or a plurality of drive shafts 328 or rollers (not shown) such that any suitable configuration can be created. It is contemplated that the supporting material can be a long, contiguous band of material having multiple peaks and valleys, or can be separate units as illustrated in FIG. 15. It will be appreciated that a single long band and a plurality of bands having any suitable relationship or configuration are contemplated.

Figure 17:
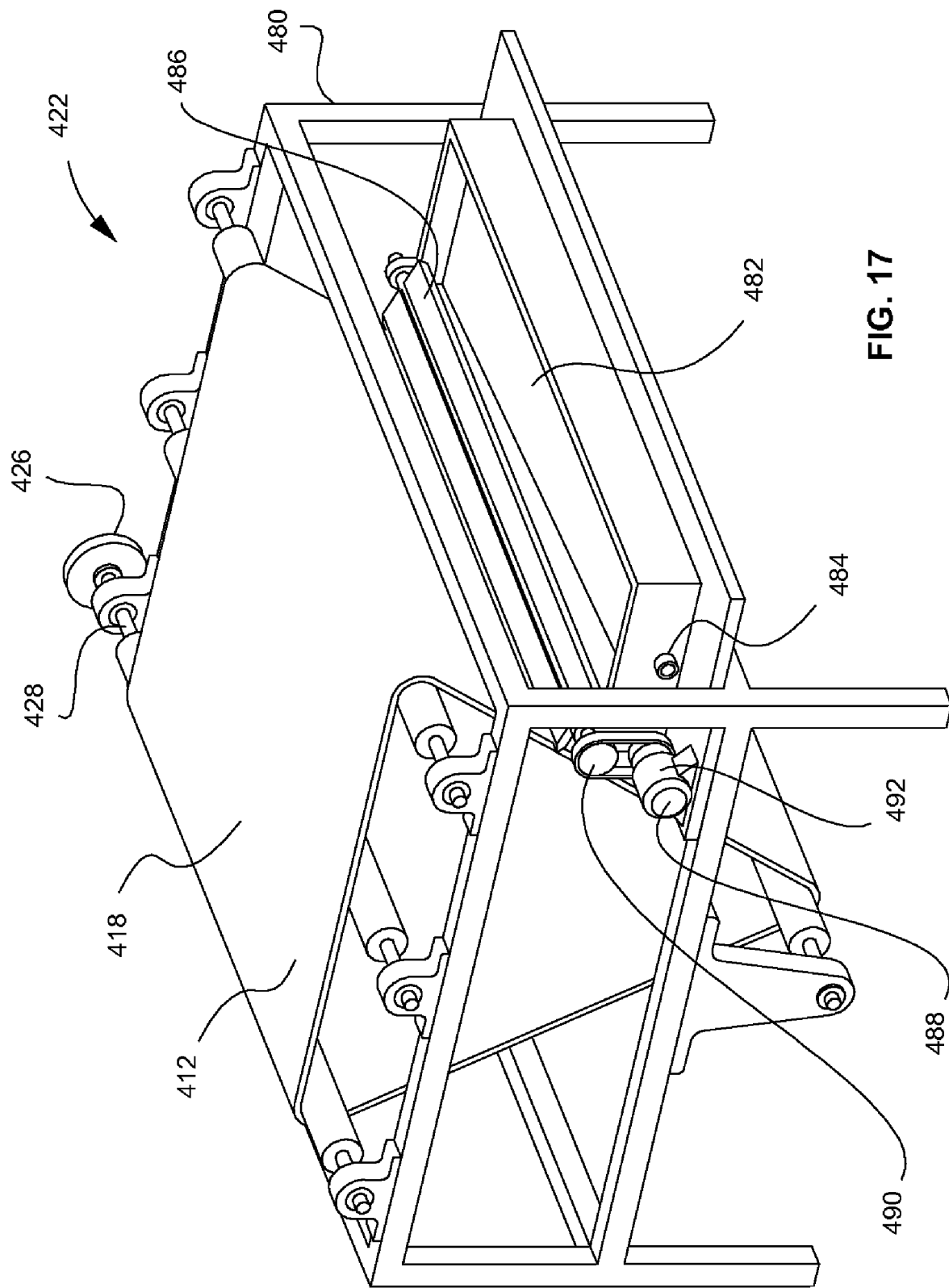
FIG. 17 depicts a perspective view of an algal growth system shown with a harvesting system according to one embodiment.

Referring to FIG. 17, an example embodiment of an algal growth system or mechanized harvesting unit 422 is shown, in which algal cells 418 can be attached to a solid surface of a supporting material 412. Embodiments of the mechanized harvesting unit 422 can include a drive motor (not shown), and a gear system 426 that can rotate one or a plurality of drive shafts 428, where the one or a plurality of drive shafts 428 can correspondingly rotate the supporting material 412, such as a flexible sheet material. Embodiments of the mechanized harvesting unit 422 can include a harvesting system 480 that can include any suitable manual or automatic harvesting mechanism and/or a harvesting reservoir 482. The harvesting system 480 can include a vacuum system 484 and a scraper 486 for harvesting the algal cells 418 from the supporting material 412. The scraper 486 can be coupled with a motor 488 and a pulley system or actuator 490 such that the scraper 486 can be selectively engaged with the supporting material 412. The motor 488 can be associated with a controller 492 such that the harvesting system 480 can be programmed to scape, harvest, or perform any other suitable function automatically or on a predetermined schedule.

Figure 20:
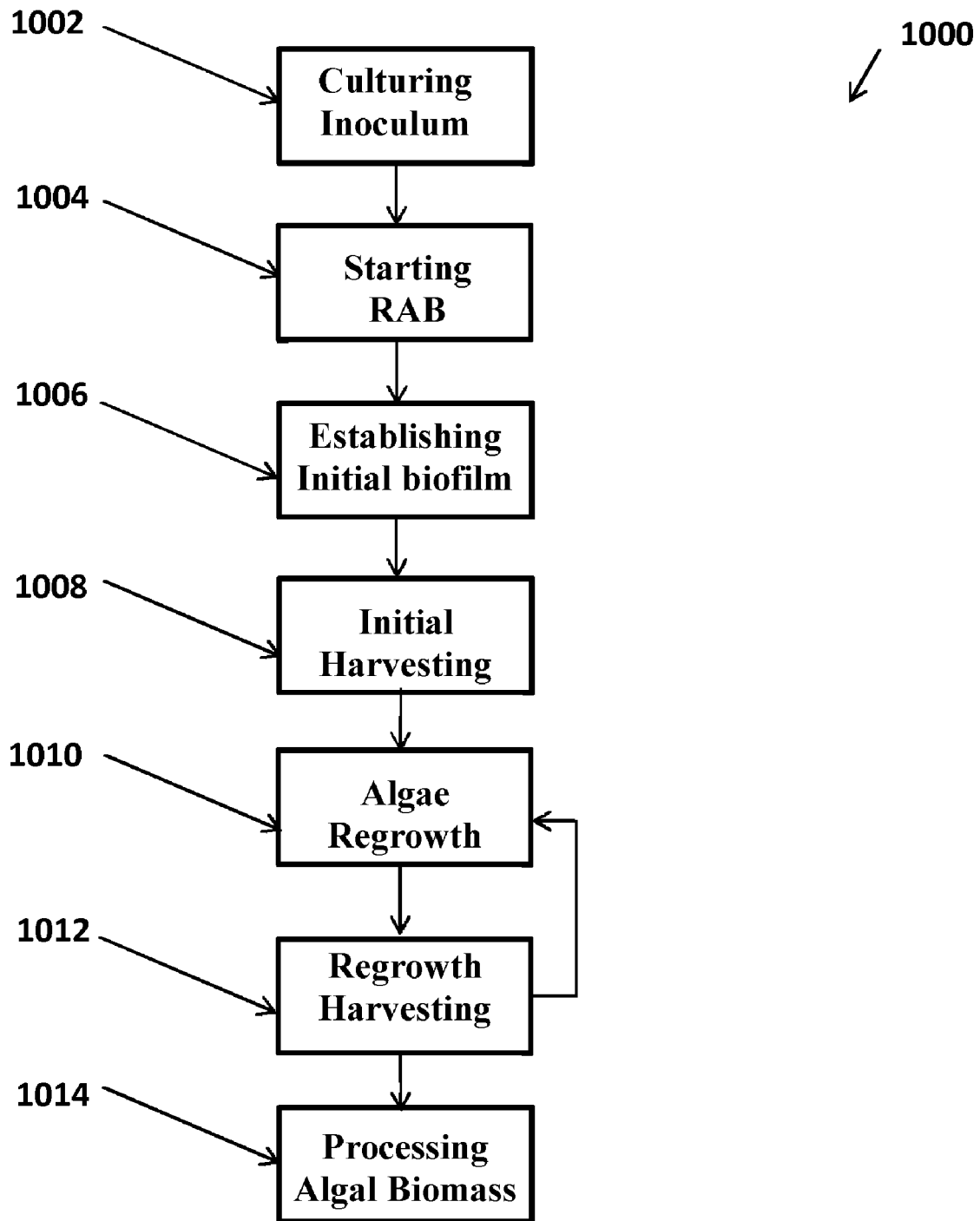
FIG. 20 depicts a flow chart showing a method for growing and harvesting algae using a raceway according to one embodiment.

FIG. 20 depicts a flow chart illustrating one example of a method 1000 that can be used for growing and/or harvesting algal cells using a raceway, such as the raceway 130 shown in FIGS. 9 and 11. The method 1000 can include Culturing Algal Inoculum 1002, which can include culturing suspended algae in an open pond, raceway, or the like, until the algal cell density is between from about 0.05 g/L to about 1.0 g/L. It will be appreciated that any suitable density of any suitable algal cells is contemplated. The method 1000 can include Starting the RAB 1004, which can include rotating or actuating the supporting material of a photobioreactor, algal growth system, mechanized harvesting unit, or the like, in accordance with versions described herein. The RAB or other suitable system can be rotated, for example, at a speed ranging from about ¼ cm/sec to about 10 cm/sec. The RAB can be rotated at from about 2 cm/sec to about 6 cm/sec. The RAB can be rotated at about 4 cm/sec. The RAB can be rotated or otherwise actuated at different speeds, which can be selectable, preprogrammed, or based on environmental conditions. Starting the RAB 1004 can include rotating the RAB system for any duration of time such as from about 5 days to about 20 days, where duration of operation can depend on the speed of the algal cells attachment on the surface of the RAB materials.

The method 1000 can include Establishing Initial Biofilm 1006, which can include the growth of algal cells on the supporting material of an RAB or photobioreactor. The initial biofilm can be deemed to be established when, for example, a threshold density of algal cells is determined. Such a threshold can be any suitable density and the density can be determined using any suitable system or method. The method 1000 can include Initial Harvesting 1008, which can include harvesting the algal biomass from the supporting material of the RAB or photobioreactor. Initial Harvesting 1008 can be accomplished by scraping the algal biofilm, vacuuming, pressurized air, or by any other suitable method.

The method 1000 can include Algae Regrowth 1010, where after harvesting, residual algal cells can remain on the supporting material surface and can automatically serve as inoculum for a next cycle of growth or regrowth. Harvesting can be performed such that a sufficient density of algal cells can be left on the supporting material to facilitate regrowth. Algae Regrowth 1010 can include operating, actuating, or rotating the algal biofilm, RAB, or photobioreactor for any suitable time period such as from about 3 days to about 8 days. The time for operating the RAB can depend, for example, on the algal species, culture conditions, rotating speed of the RAB system, the liquid fluid rate reservoir, or any other suitable factor. Method 1000 can include Regrowth Harvesting 1012, which can include harvesting the algal biofilm that has accumulated on the supporting material. The method 1000 can include repeating Algae Regrowth 1010 and Regrowth Harvesting 1012 for as many times as appropriate. The system can operate substantially indefinitely, or can be periodically interrupted for cleaning or for other reasons. The method 1000 can include Processing Algal Biomass 1014, which can include processing the harvested algae by, for example, drying and extracting oil from the harvested algal cells. It will be appreciated that any suitable processing is contemplated.

Figure 19:
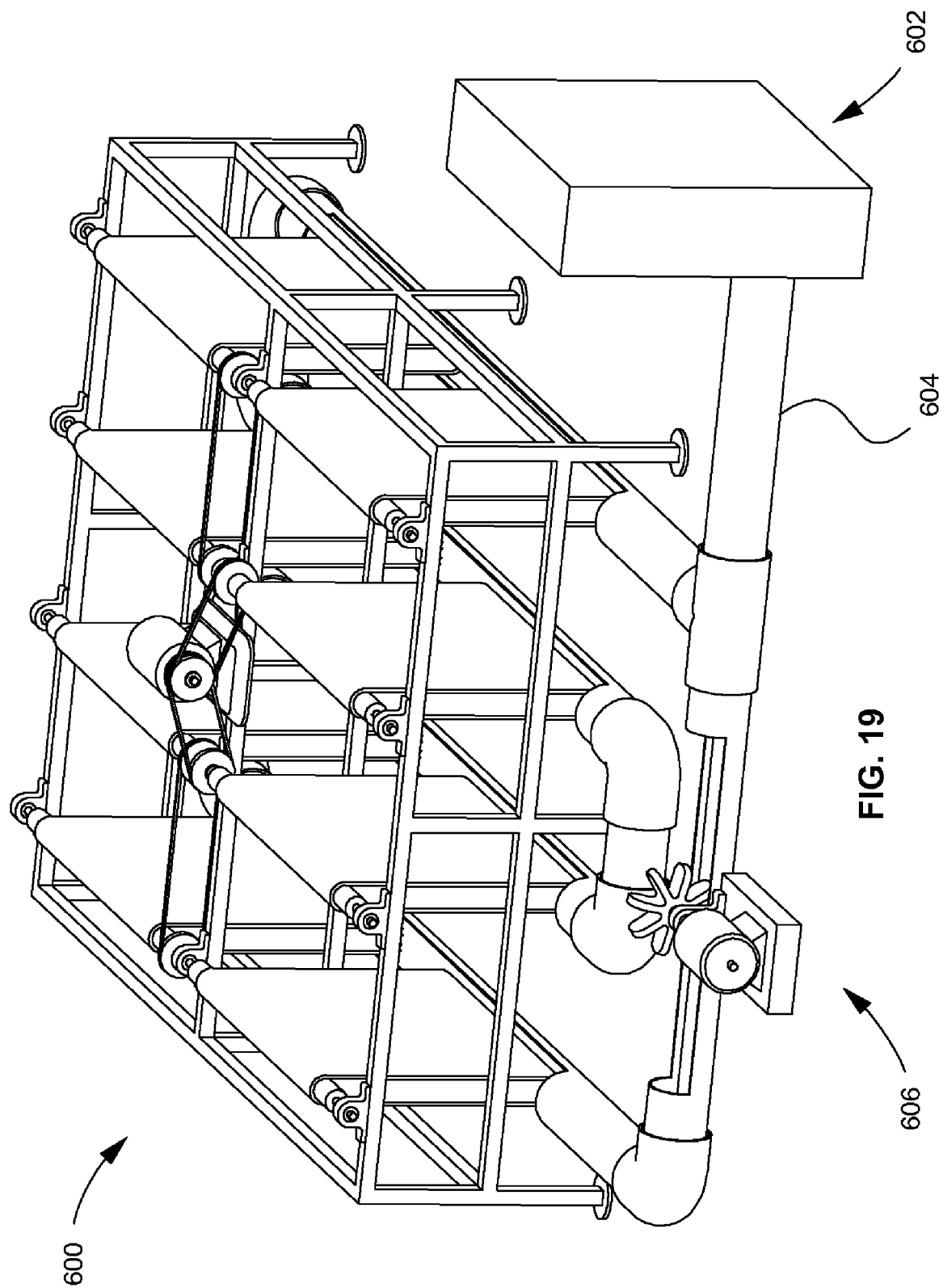
FIG. 19 depicts a perspective view of a photobioreactor according to one embodiment.
Figure 21:
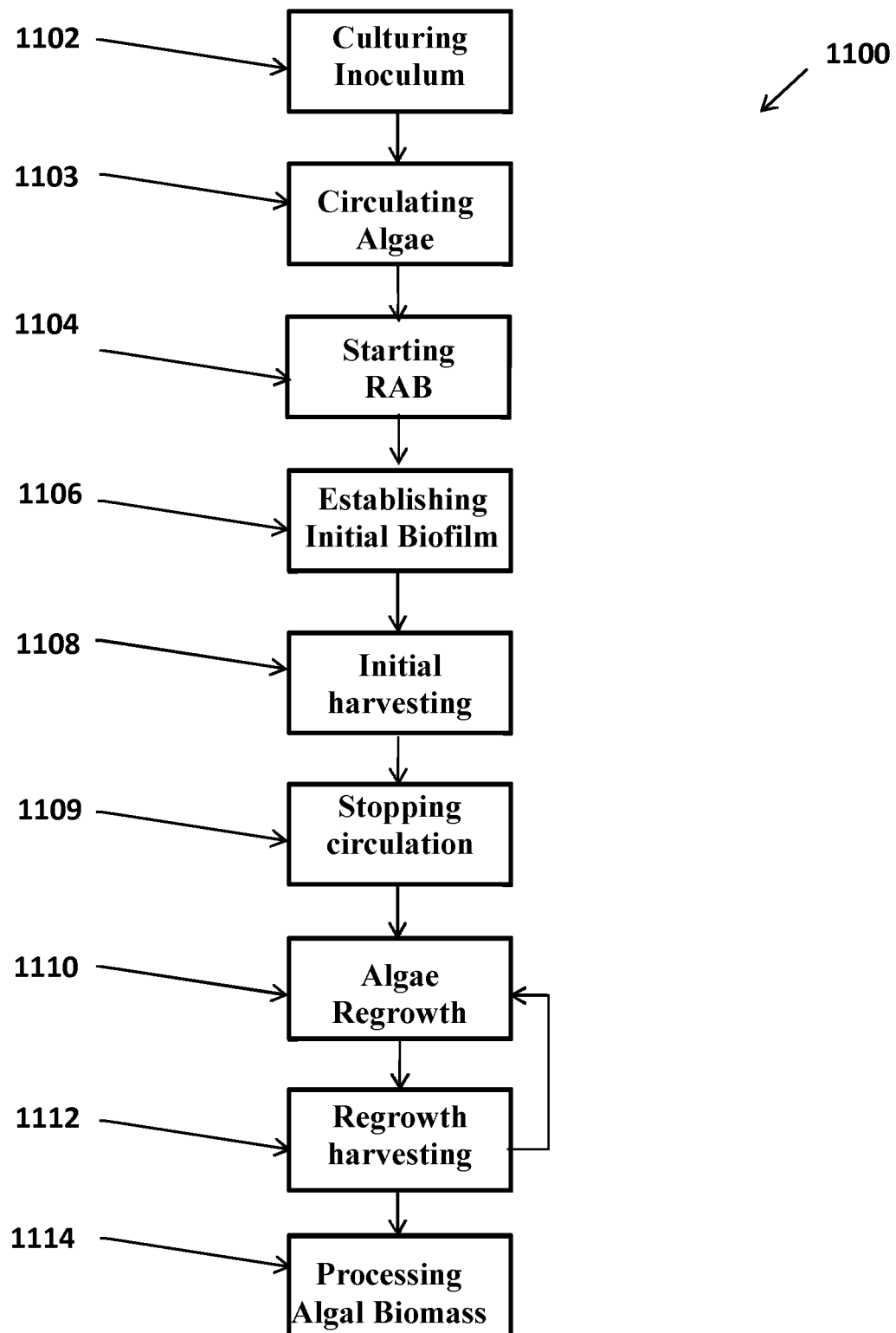
FIG. 21 depicts a flow chart showing a method for growing and harvesting algae using a trough according to one embodiment.

FIG. 21 depicts a flow chart illustrating one example of a method 1100 that can be used for growing and/or harvesting algal cells, such as with a photobioreactor 600 shown in FIG. 19, a trough, a partially enclosed fluid reservoir, or other suitable bioreactor. In such a system, it may be beneficial to seed or otherwise provide algal cells grown at a first location 602 (FIG. 19) and transport the algal cells via a channel 604 (FIG. 19), or other suitable connection, to a second location 606 (FIG. 19), such as to a photobioreactor provided in accordance with versions described herein. The first location can be fluidly coupled to the second location or, in an alternate embodiment, the first location can be a portable bioreactor that can be selectively connected to the second location as needed.

The method 1100 can include Culturing Algal Inoculum 1102, which can include culturing suspended algae in an open pond, portable photobioreactor, or the like, at the first location until the algal cell density is between, for example, from about 0.05 g/L to about 3.0 g/L. It will be appreciated that any suitable density of any suitable algal cells is contemplated, although in one embodiment the cell density can be higher than in an open raceway system, where the reduction of light in a trough system may benefit from a higher initial cell density. The method 1100 can include Circulating Algae 1103, which can include providing or otherwise delivering the algal cells from the first location to the trough or partially enclosed system, which can include generating a fluid dynamic or flow such that algal cells from the first growth region are transitioned to the trough in the second region. The method 1100 can include Starting the RAB 1104, which can include rotating or actuating the supporting material of a photobioreactor, algal growth system, mechanized harvesting unit, or the like, in accordance with versions described herein. The RAB or other suitable system can be rotated, for example, at a speed ranging from about ¼ cm/sec to about 10 cm/sec. The RAB can be rotated at from about 2 cm/sec to about 6 cm/sec. The RAB can be rotated at about 4 cm/sec. The RAB can be rotated or otherwise actuated at different speeds, which can be selectable, preprogrammed, or based on environmental conditions. Starting the RAB 1104 can include rotating the RAB system for any duration of time such as from about 5 days to about 20 days, where duration of operation can depend on the speed of the algal cells attachment on the surface of the RAB materials.

The method 1100 can include Establishing Initial Biofilm 1106, which can include the growth of algal cells on the supporting material of an RAB or photobioreactor. The initial biofilm can be deemed to be established when, for example, a threshold density of algal cells is determined. Such a threshold can be any suitable density and the density can be determined using any suitable system or method. The method 1000 can include Initial Harvesting 1108, which can include harvesting the algal biomass from the supporting material of the RAB or photobioreactor. Initial Harvesting 1008 can be accomplished by scraping the algal biofilm, vacuuming, pressurized air, or by any other suitable method.

The method 1100 can include Stopping Circulation 1109, which can include stopping delivery of algal cells from the first growth location to the second trough location, for example. In one embodiment, once the RAB is seeded with algal cells, the RAB may no longer need to be seeded or otherwise infused with additional algal cells for subsequent regrowth and harvesting steps. It will be appreciated that a feeder or seeding system for algal cells can be reattached or can be maintained throughout if desirable. The method 1100 can include Algae Regrowth 1110, where after harvesting, residual algal cells can remain on the supporting material surface and can automatically serve as inoculum for a next cycle of growth or regrowth. Harvesting can be performed such that a sufficient density of algal cells can be left on the supporting material to facilitate regrowth. Algae Regrowth 1110 can include operating, actuating, or rotating the algal biofilm, RAB, or photobioreactor for any suitable time period such as from about 3 days to about 8 days. The time for operating the RAB can depend, for example, on the algal species, culture conditions, rotating speed of the RAB system, the liquid fluid rate of the reservoir, the type of reservoir, or any other suitable factor. Method 1100 can include Regrowth Harvesting 1112, which can include harvesting the algal biofilm that has accumulated on the supporting material. The method 1100 can include repeating Algae Regrowth 1110 and Regrowth Harvesting 1112 for as many times as appropriate. The system can operate substantially indefinitely, or can be periodically interrupted for cleaning or for other reasons. The method 1100 can include Processing Algal Biomass 1114, which can include processing the harvested algae by, for example, drying and extracting oil from the harvested algal cells. It will be appreciated that any suitable processing is contemplated.

In various embodiments disclosed herein, a single component can be replaced by multiple components and multiple components can be replaced by a single component to perform a given function or functions. Except where such substitution would not be operative, such substitution is within the intended scope of the embodiments.

Some of the figures can include a flow diagram. Although such figures can include a particular logic flow, it can be appreciated that the logic flow merely provides an exemplary implementation of the general functionality. Further, the logic flow does not necessarily have to be executed in the order presented unless otherwise indicated. In addition, the logic flow can be implemented by a hardware element, a software element executed by a computer, a firmware element embedded in hardware, or any combination thereof.

The foregoing description of embodiments and examples has been presented for purposes of illustration and description. It is not intended to be exhaustive or limiting to the forms described. Numerous modifications are possible in light of the above teachings. Some of those modifications have been discussed, and others will be understood by those skilled in the art. The embodiments were chosen and described in order to best illustrate principles of various embodiments as are suited to particular uses contemplated. The scope is, of course, not limited to the examples set forth herein, but can be employed in any number of applications and equivalent devices by those of ordinary skill in the art. Rather it is hereby intended the scope of the invention to be defined by the claims appended hereto.

What is claimed is:

1. A biomass growth system comprising:
   a. a frame;
   b. a first flexible sheet material mounted on a first frame in a first mounted geometry having a first height and a first width, wherein the first height is greater than the first width;
   c. a second flexible sheet material mounted on a second frame in a second mounted geometry having a second height and a second width, the first flexible sheet material and the second flexible sheet material being noncontiguous, wherein the second height is greater than the second width;
   d. a first drive shaft, the first drive shaft being coupled with the first frame, wherein the first drive shaft actuates the first flexible sheet material, and a second drive shaft, the second drive shaft being coupled with the second frame, wherein the second drive shaft actuates the second flexible sheet material;
   e. an actuator system, wherein the actuator system is coupled with the first drive shaft and the second drive shaft such that the first flexible sheet material and the second flexible sheet material are concurrently actuated;
   f. a motor, the motor being coupled with the actuator system, wherein the motor actuates the actuator system and the first drive shaft such that the first flexible sheet material is actuated and the second drive shaft such that the second flexible sheet material is actuated concurrently;
   g. a harvesting mechanism; and
   h. a reservoir, at least a portion of the reservoir being positioned beneath the frame.

2. The biomass growth system of claim 1, wherein the harvesting mechanism is an automatic harvesting mechanism.

3. The biomass growth system of claim 1, wherein the first flexible sheet material and the second flexible sheet material are selected from the group consisting of cheesecloth, fiberglass, porous PTFE coated fiberglass, chamois, vermiculite, microfiber, synthetic chamois, burlap, cotton duck, velvet, poly-lactic acid, abrased poly-lactic acid, vinyl laminated nylon, polyester, wool, acrylic, lanolin, woolen, cashmere, leather, silk, lyocell, hemp fabric, polyurethane, olefin fibre, polylactide, carbon fiber, and combinations thereof.

4. The biomass growth system of claim 1, wherein the harvesting mechanism is operably configured to harvest biomass comprising algae or fungi.

5. The biomass growth system of claim 1, wherein the harvesting mechanism is operably configured to harvest biomass comprising a prokaryotic organism or a eukaryotic organism.

6. The biomass growth system of claim 1, wherein the motor is associated with a programmable controller that is operably configured to rotate the first flexible sheet material and the second flexible sheet material on a predetermined schedule.

7. The biomass growth system of claim 1, wherein each of the first flexible sheet material and the second flexible sheet material comprises a surface roughness, a hydrophobicity, and a positive surface charge.

8. The biomass growth system of claim 1, wherein the reservoir includes an amount of contacting liquid.

9. A biomass growth system comprising:
   a. a first flexible sheet material mounted on a first frame in a first mounted geometry having a first height and a first width, wherein the first height is greater than the first width;
   b. a second flexible sheet material mounted on a second frame in a second mounted geometry having a second height and a second width, the first flexible sheet material and the second flexible sheet material being noncontiguous, wherein the second height is greater than the second width;
   c. a drive motor, the drive motor being coupled with a gear system, wherein the drive motor actuates the gear system such that the first flexible sheet material and the second flexible sheet material are actuated concurrently; and
   d. a raceway, at least a portion of the raceway being positioned beneath the first flexible sheet material and the second flexible sheet material.

10. The biomass growth system of claim 9, wherein the first flexible sheet material and the second flexible sheet material are selected from the group consisting of cheesecloth, fiberglass, porous PTFE coated fiberglass, chamois, vermiculite, microfiber, synthetic chamois, burlap, cotton duck, velvet, poly-lactic acid, abrased poly-lactic acid, vinyl laminated nylon, polyester, wool, acrylic, lanolin, woolen, cashmere, leather, silk, lyocell, hemp fabric, polyurethane, olefin fibre, polylactide, carbon fiber, and combinations thereof.

11. The biomass growth system of claim 9, further comprising a harvesting mechanism operably configured to harvest biomass comprising algae or fungi.

12. The biomass growth system of claim 9, further comprising a harvesting mechanism operably configured to harvest biomass comprising a prokaryotic organism or a eukaryotic organism.

13. The biomass growth system of claim 9, wherein the drive motor is associated with a programmable controller that is configured to rotate the first flexible sheet material and the second flexible sheet material on a predetermined schedule.

14. The biomass growth system of claim 9, wherein each of the first flexible sheet material and the second flexible sheet material comprises a surface roughness, a hydrophobicity, and a positive surface charge.

15. The biomass growth system of claim 9, wherein the raceway includes an amount of contacting liquid.

16. A biomass growth system comprising:
   a. a first flexible sheet material mounted on a first frame in a first mounted geometry having a first height and a first width, wherein the first height is greater than the first width;
   b. a second flexible sheet material mounted on a second frame in a second mounted geometry having a second height and a second width, the first flexible sheet material and the second flexible sheet material being noncontiguous, wherein the second height is greater than the second width;
   c. a motor, the motor being coupled with an actuator system, wherein the motor is operably configured to actuate the actuator system such that the first flexible sheet material and the second flexible sheet material are actuated concurrently; and
   d. a reservoir, at least a portion of the reservoir being positioned beneath the first frame and the second frame.

17. The biomass growth system of claim 16, further comprising a harvesting mechanism.

18. The biomass growth system of claim 16, wherein the first flexible sheet material and the second flexible sheet material are selected from the group consisting of cheesecloth, fiberglass, porous PTFE coated fiberglass, chamois, vermiculite, microfiber, synthetic chamois, burlap, cotton duck, velvet, poly-lactic acid, abrased poly-lactic acid, vinyl laminated nylon, polyester, wool, acrylic, lanolin, woolen, cashmere, leather, silk, lyocell, hemp fabric, polyurethane, olefin fibre, polylactide, and carbon fiber.

19. The biomass growth system of claim 16, wherein the motor is associated with a programmable controller.

20. The biomass growth system of claim 16, wherein the reservoir includes an amount of contacting liquid.

* * * * *